(12) United States Patent
Boudreaux et al.

(10) Patent No.: US 7,481,824 B2
(45) Date of Patent: *Jan. 27, 2009

(54) SURGICAL INSTRUMENT WITH BENDING ARTICULATION CONTROLLED ARTICULATION PIVOT JOINT

(75) Inventors: Chad P. Boudreaux, Cincinnati, OH (US); Douglas J. Siebenaler, Maineville, OH (US); Geoffrey C. Hueil, Mason, OH (US); Kenneth E. Hogue, Mason, OH (US); Christoph L. Gillum, Middletown, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 111 days.

This patent is subject to a terminal disclaimer.

(21) Appl. No.: 11/323,536

(22) Filed: Dec. 30, 2005

(65) Prior Publication Data

US 2007/0152014 A1 Jul. 5, 2007

(51) Int. Cl.
*A61B 17/00* (2006.01)
*A61B 1/00* (2006.01)
*A61M 39/10* (2006.01)
*B25J 17/02* (2006.01)

(52) U.S. Cl. .................. 606/205; 600/146; 604/533; 74/490.06; 901/29

(58) Field of Classification Search ........... 606/205, 606/170; 600/146; 285/282, 272; 604/533–537; 901/25, 26, 29; 74/469, 490.01, 490.05, 74/490.06; 294/19.1, 19.3, 116

See application file for complete search history.

(56) References Cited

U.S. PATENT DOCUMENTS

| | | | | |
|---|---|---|---|---|
| 4,983,165 | A | * | 1/1991 | Loiterman ............... 604/95.03 |
| 5,245,885 | A | * | 9/1993 | Robertson ............... 74/490.01 |
| 5,465,895 | A | | 11/1995 | Knodel et al. |
| 5,826,776 | A | * | 10/1998 | Schulze et al. ........... 227/176.1 |
| 2004/0232196 | A1 | | 11/2004 | Shelton et al. |
| 2005/0070958 | A1 | | 3/2005 | Swayze et al. |
| 2006/0047303 | A1 | * | 3/2006 | Ortiz et al. .................. 606/205 |

\* cited by examiner

*Primary Examiner*—Kevin T Truong
*Assistant Examiner*—Katherine M Dowe
(74) *Attorney, Agent, or Firm*—Frost Brown Todd LLC

(57) ABSTRACT

A surgical instrument particularly suited to endoscopic and laparoscopic insertion through a cannula of a trocar into an insufflated body cavity or lumen includes a bending member in an elongate shaft that acts to rotate an end effector about an articulation pivot joint. A proximally directed camming surface (e.g., gear segment, cam recess) aft of a pivotal attachment of the end effector to a proximal frame ground of the elongate shaft interacts with a bending member whose proximal end is ground to the proximal frame ground. Differential fluidic actuators or mechanical cam bars deflect a distal end (e.g., rack, cam point) of the bending member to effect articulation. Thereby, the end effector may act upon tissue that would otherwise be obscured, such as behind an organ. The articulated end effector also advantageously allows an endoscope to be positioned behind the end effector without being blocked by the instrument shaft.

16 Claims, 21 Drawing Sheets

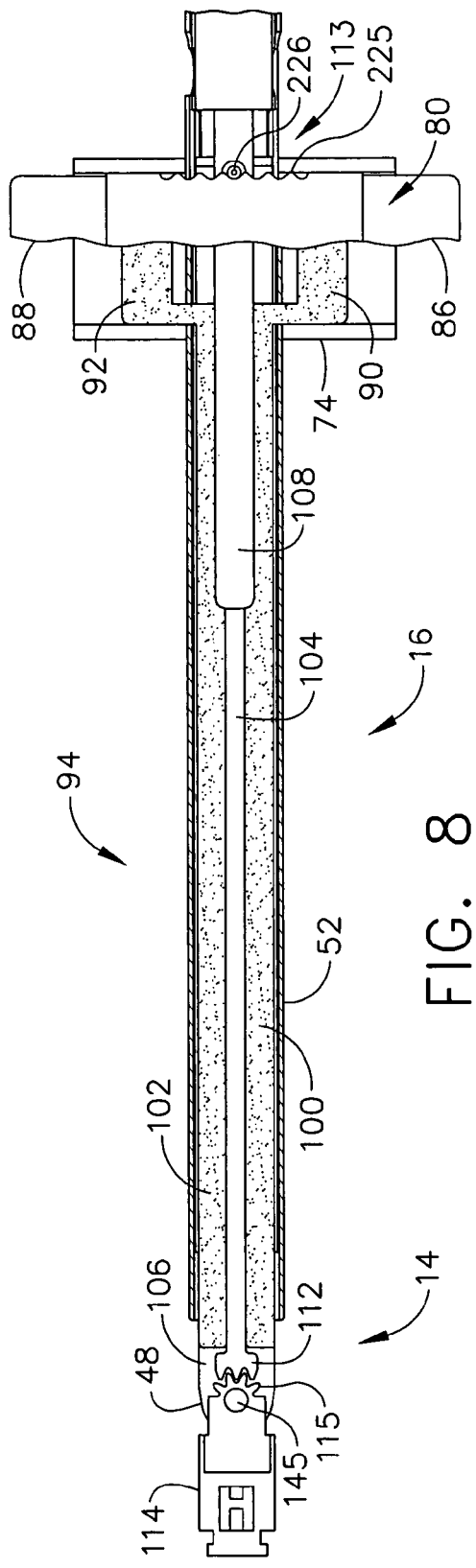
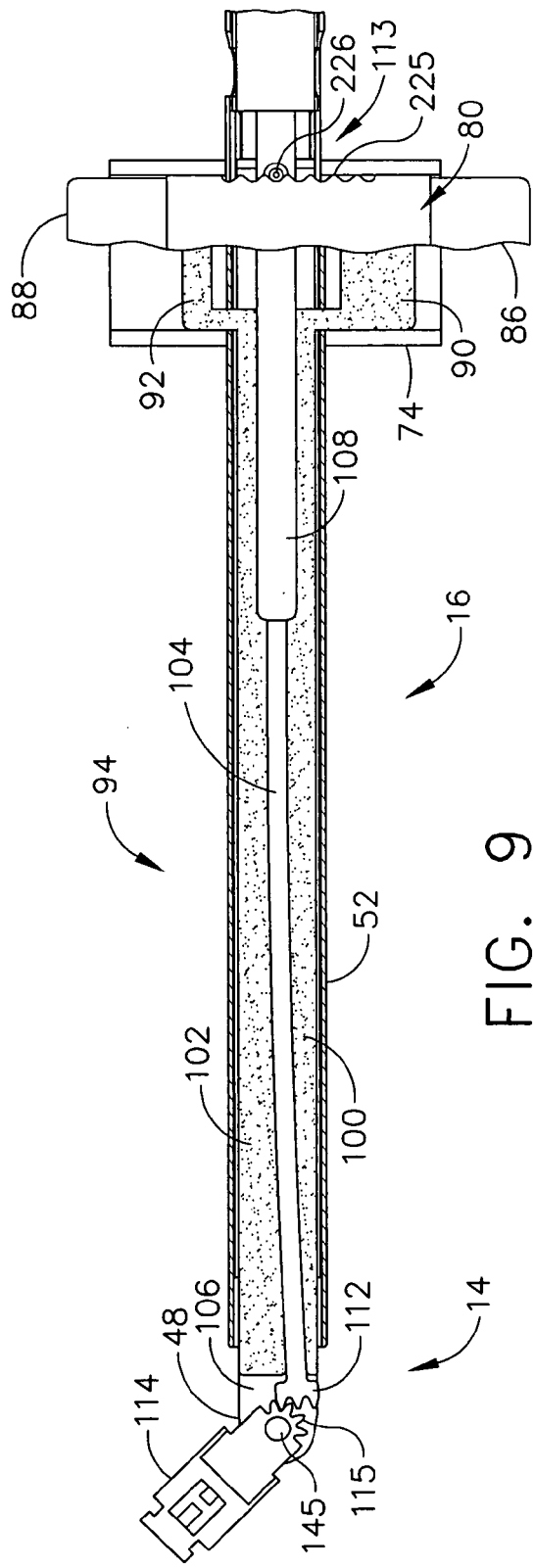

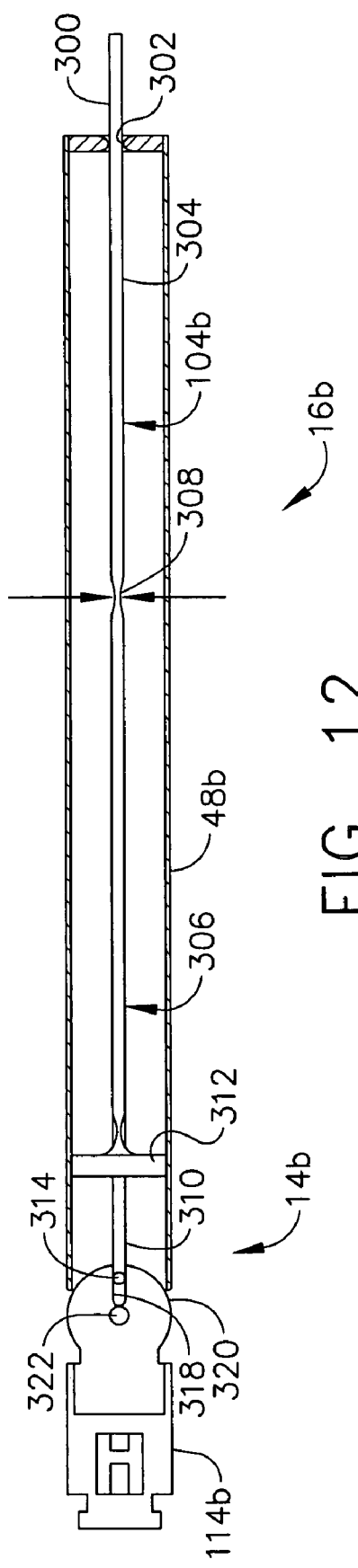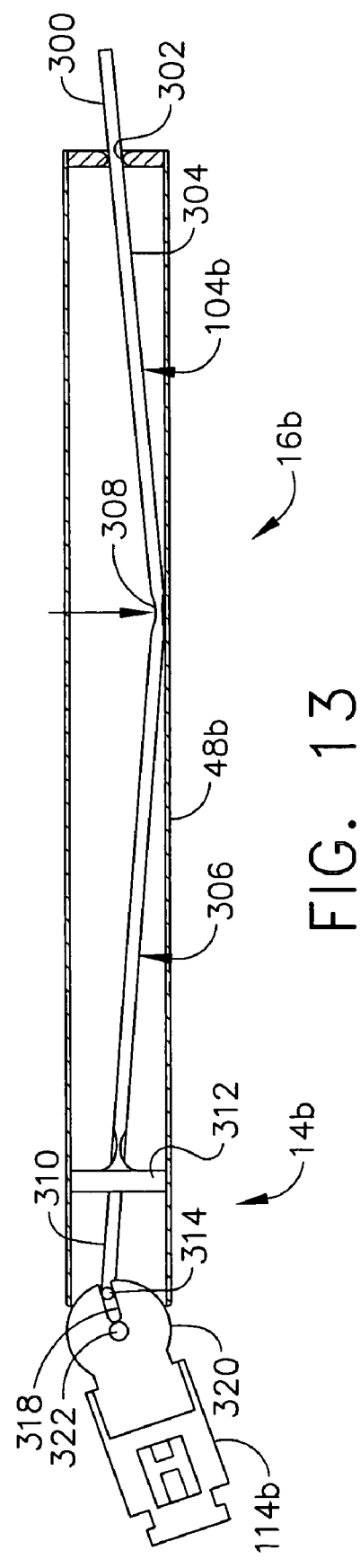

SURGICAL INSTRUMENT WITH BENDING ARTICULATION CONTROLLED ARTICULATION PIVOT JOINT

REFERENCE TO RELATED APPLICATION

The present invention is related to commonly owned U.S. patent application Ser. No. 11/061,908 entitled "SURGICAL INSTRUMENT INCORPORATING A FLUID TRANSFER CONTROLLED ARTICULATION MECHANISM" to Kenneth Wales and Chad Boudreaux filed on Feb. 18, 2005, the disclosure of which is hereby incorporated by reference in its entirety.

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and an energy device using ultrasound, RF, laser, etc.) to a surgical site, and more particularly to such surgical instruments with an articulating shaft.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures have been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Positioning the end effector is constrained by the trocar. Generally, these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument.

While these mechanically communicated articulation motions have successfully enabled an endoscopic surgical stapling and severing instrument to articulate, development trends pose numerous challenges and barriers to entry into the market. Conflicting design objects include a shaft of as small a diameter as possible to reduce the size of the surgical opening yet with sufficient strength to perform the several motions (e.g., closing, firing, articulation, rotation, etc.). In addition, transferring sufficient force without binding and other frictional problems imposes design constraints that limit desirable features and reliability.

Consequently, a significant need exists for an articulating surgical instrument that incorporates an articulation mechanism that employs an articulation force that may be incorporated within the close confines thereof without interfering with the firing and closing motions.

BRIEF SUMMARY OF THE INVENTION

The invention overcomes the above-noted and other deficiencies of the prior art by providing a surgical instrument having an articulating shaft attached between a handle and an end effector that uses a bending member grounded in a proximal portion of the shaft that acts against a pivoting feature of the end effector. Laterally moving actuators on opposing sides of the bending member control the pivoting to each side. This bending moving member presents a large longitudinal surface area to act upon differentially, advantageously achieving a desired force to articulate within close confines of an elongate shaft suitable for insertion through a cannula of a trocar for endoscopic or laparoscopic surgical procedures.

In one aspect of the invention, a surgical instrument has an end effector with a proximal camming surface. A bending member has a proximal end grounded to a frame within a lateral recess of a frame and a distal end that engages the proximal camming surface. Thus, as an articulation control actuator proximally attached to the elongate shaft deflects the distal end of the bending member, the end effector articulates about its pivotal attachment to the frame of the elongate shaft.

In another aspect of the invention, the surgical instrument includes differential actuators that are opposingly positioned against the proximal camming surface of the end effector such that an articulation control actuator proximally attached to the elongate shaft differentially actuates the differential actuators to selectively deflect a distal end of the bending member to articulate the end effector.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above and the detailed description of the embodiments given below, serve to explain the principles of the present invention.

FIG. 8 is a top view of the first version of the bending articulation mechanism including differential fluidic actuation of FIG. 7 in a nonarticulated state with a lateral compression channel partially cut away to expose reservoir bladders.

FIG. 9 is a top view of the first version of the bending articulation mechanism of FIG. 7 in a rightward articulated state.

FIG. 12 is a top view of a third version of a bending articulation mechanism for the surgical stapling and severing instrument with a compound bending member depicted in a nonarticulated state.

FIG. 13 is a top view of the third version of the bending articulation mechanism of FIG. 12 depicted with the compound bending member in an articulated state.

DETAILED DESCRIPTION OF THE INVENTION

Figure 1:
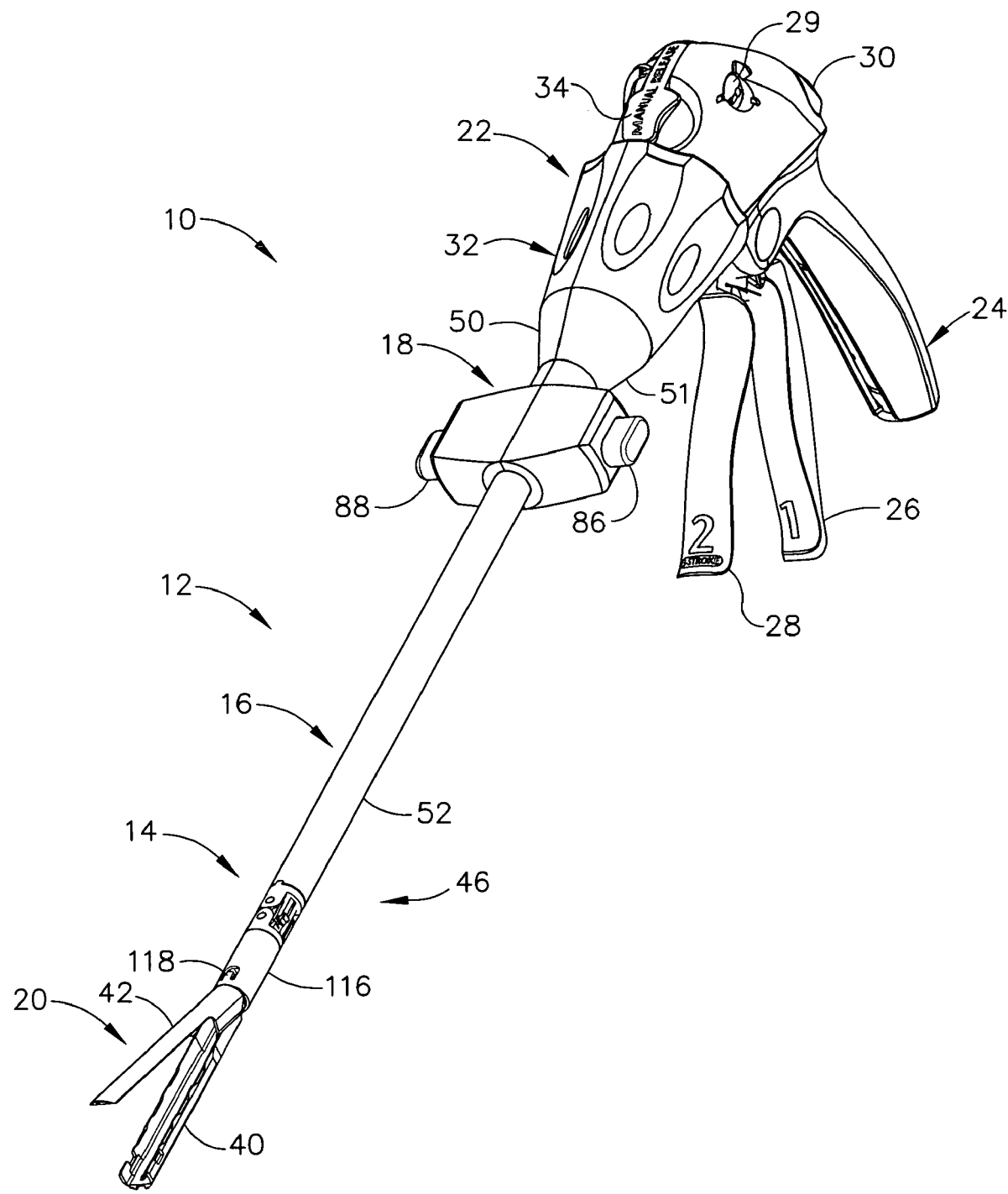
FIG. 1 is a front top perspective view of a surgical stapling and severing instrument shown with an open end effector, or staple applying assembly, and with the staple cartridge removed.

Turning to the Drawings, wherein like numerals denote like components throughout the several views, FIG. 1 depicts a surgical instrument, which in the illustrative versions is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to an insufflated body cavity or lumen (surgical site) in a patient (not shown) for performing a surgical procedure. Once an implement portion 12 is inserted through a cannula passageway, a bending articulation mechanism 14 incorporated into a distal portion of an elongate shaft 16 of the implement portion 12 may be remotely articulated (i.e., external to the patient), as depicted in FIG. 2, by an articulation control 18.

An end effector, depicted in the illustrative version as a staple applying assembly 20, is distally attached to the bending articulation mechanism 14. Thus, remotely articulating the bending articulation mechanism 14 thereby articulates the staple applying assembly 20 from a longitudinal axis of the elongate shaft 16. Such an angled position may have advantages in approaching tissue from a desired angle for severing and stapling, approaching tissue otherwise obstructed by other organs and tissue, and/or allowing an endoscope to be positioned behind and aligned with the staple applying assembly 20 for confirming placement.

The surgical stapling and severing instrument 10 includes a handle portion 22 proximally connected to the implement portion 12 for providing positioning, articulation, closure and firing motions thereto. The handle portion 22 includes a pistol grip 24 toward which a closure trigger 26 is pivotally and proximally drawn by the clinician to cause clamping or closing of the staple applying assembly 20. A firing trigger 28 is farther outboard of the closure trigger 26 and is pivotally drawn by the clinician to cause the stapling and severing of tissue clamped in the staple applying assembly 20. The illustrative version reduces the required force to squeeze the firing trigger by distributing the firing force over multiple firing strokes with firing progress indicated by a firing gauge 29 on the handle portion 20. Thereafter, a closure release button 30 is depressed to release the clamped closure trigger 26, and thus the severed and stapled ends of the clamped tissue. The handle portion 22 also includes a rotation knob 32 coupled for movement with the elongate shaft 16 to rotate the shaft 16 and the articulated staple applying assembly 20 about the longitudinal axis of the shaft 16. The handle portion 22 also includes a firing retraction handle 34 to assist in retracting a firing mechanism (not depicted) should binding occur, so that opening of the staple applying assembly 20 may occur thereafter.

Figure 2:
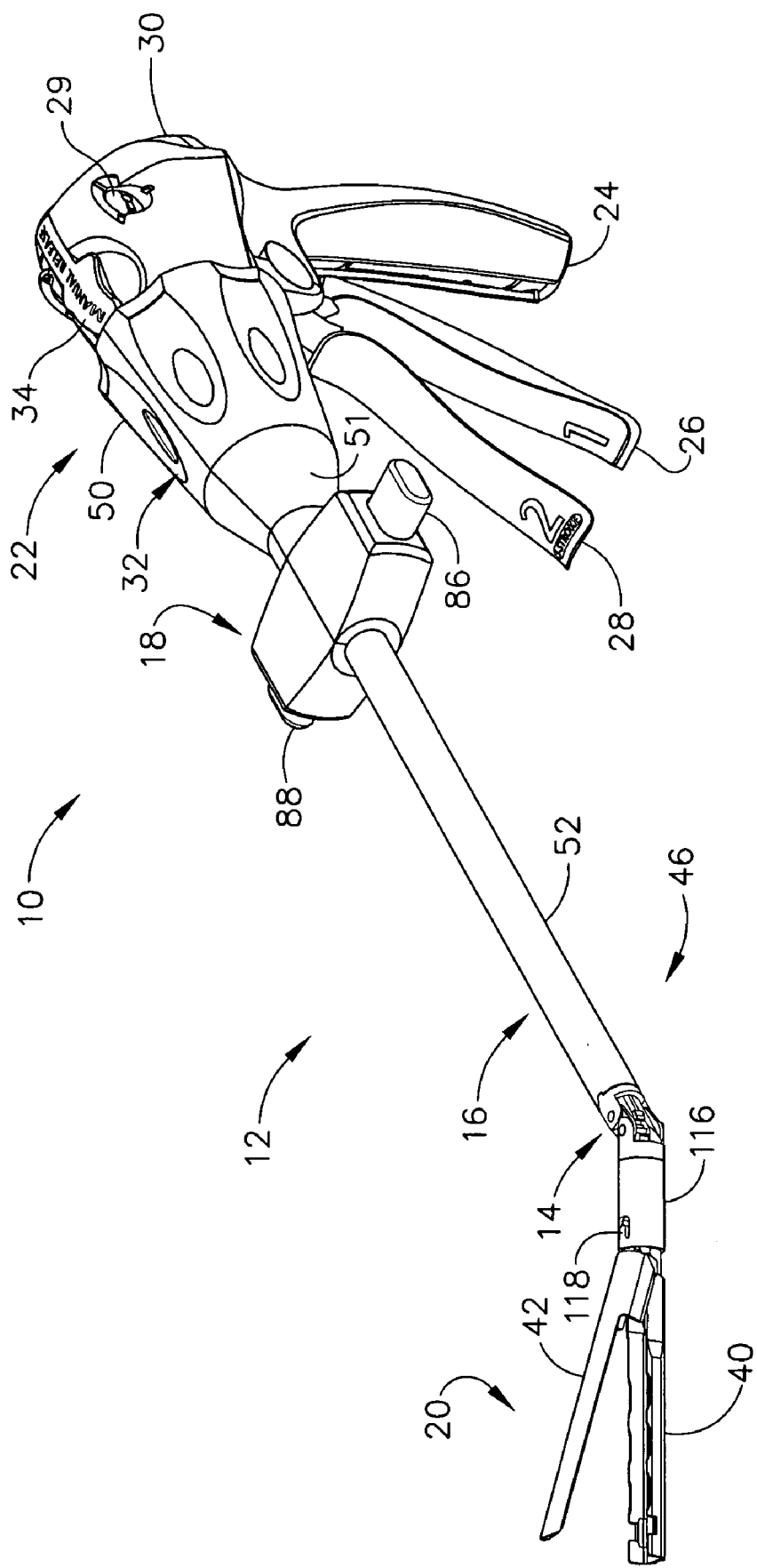
FIG. 2 is a front top perspective view of the surgical stapling and severing instrument of FIG. 1 with an articulation mechanism.

An illustrative multi-stroke handle portion 22 for the surgical stapling and severing instrument 10 of FIGS. 1-2 is described in greater detail in the co-pending and commonly-owned U.S. patent application Ser. No. 10/674,026, entitled "SURGICAL STAPLING INSTRUMENT INCORPORATING A MULTISTROKE FIRING POSITION INDICATOR AND RETRACTION MECHANISM" to Swayze and Shelton IV, the disclosure of which is hereby incorporated by reference in its entirety, with additional features and variation as described herein. While a multi-stroke handle portion 22 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgarn, Ser. No. 10/441,632, the disclosure of which is hereby incorporated by reference in its entirety.

In FIGS. 3-6, the implement portion 12 advantageously incorporates the multiple actuation motions of longitudinal rotation, articulation, closure and firing within a small diameter suitable for endoscopic and laparoscopic procedures. The staple applying assembly 20 ("end effector") has a pair of pivotally opposed jaws, depicted as an elongate staple channel 40 with a pivotally attached anvil 42 (FIGS. 1-2, 4-5). Closure and clamping of the anvil 42 to the elongate staple channel 40 is achieved by longitudinally supporting the elongate staple channel 40 with a frame assembly 44 (FIG. 3) rotatingly attached to the handle portion 22 over which a double pivot closure sleeve assembly 46 longitudinally moves to impart a closing and opening respectively to a distal and proximal motion to the anvil 42, even with the staple applying assembly 20 articulated as in FIG. 2.

Figure 3:
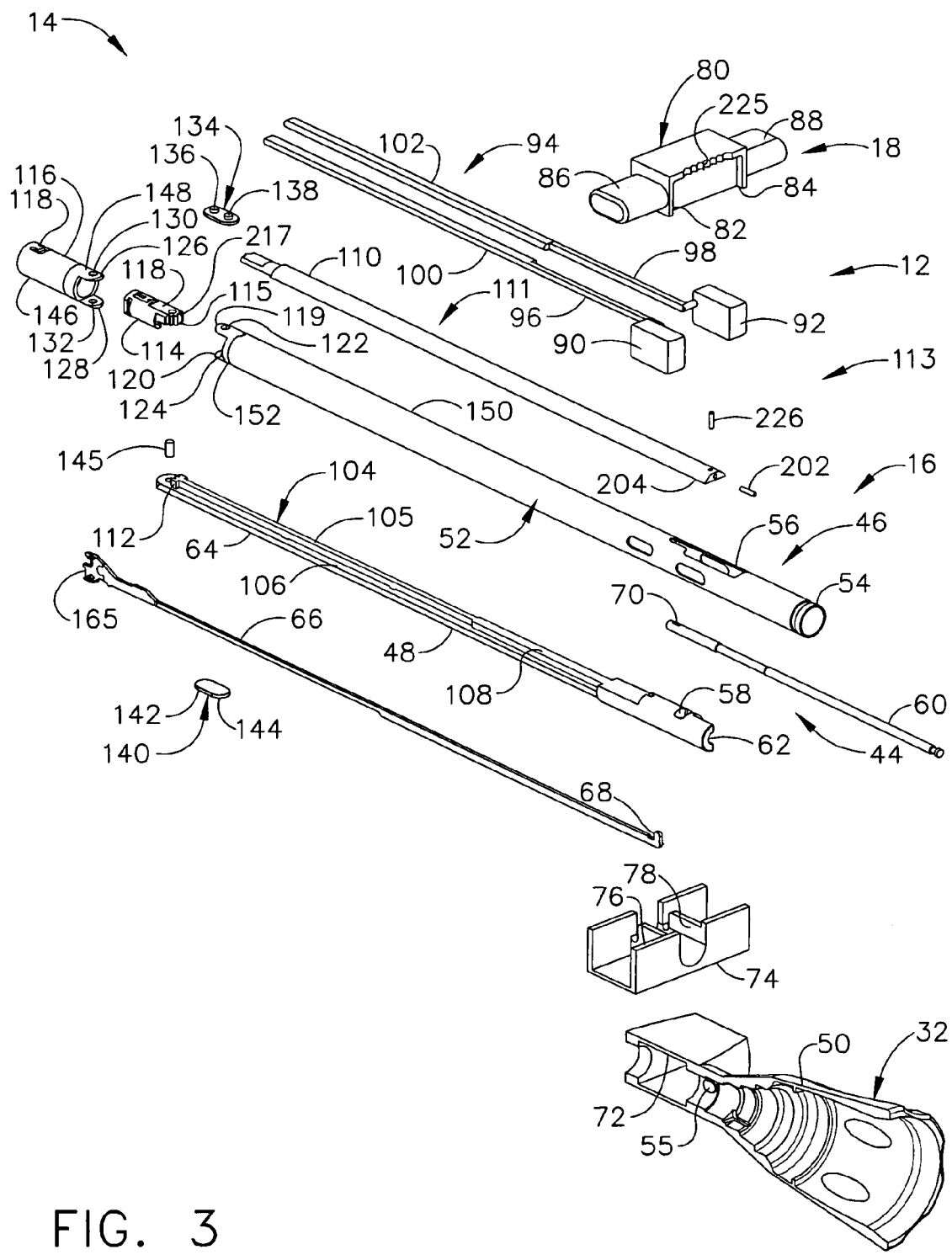
FIG. 3 is a left aft perspective disassembled view of an elongate shaft and articulation mechanism of the surgical stapling and severing instrument of FIG. 1.

With particular reference to FIG. 3, the frame assembly 44 includes a single pivot frame ground 48 whose proximal end is rotatably engaged to the handle portion 22. The rotation knob 32 is also rotatably engaged to the handle portion 22 to rotate single pivot frame ground 48. A right half shell 50 is depicted in FIG. 3 with the assembled right half shell 50 with a rotation knob left half shell 51 depicted in FIGS. 1-2. It should be appreciated that a proximal end of the closure sleeve assembly 46, specifically of a closure straight tube 52, encompasses the proximal end of the frame ground 48, passing further internally to the handle portion 22 to engage closure components (not shown) that longitudinally translate the closure sleeve assembly 46. A circular lip 54 at the proximal end of the closure straight tube 52 provides a rotating engagement to such components. Engaging features 55 of the rotation knob 32 pass through a longitudinal slot 56 on a proximal portion of the straight closure tube 52 to engage an aperture 58 proximally positioned on the frame ground 48. The longitudinal slot 56 is of sufficient longitudinal length to allow the closure longitudinal translation of the closure sleeve assembly 46 at various rotational angles set by the rotation knob 32 to the closure sleeve assembly 46 and the frame ground 48.

The elongate shaft 16 supports the firing motion by receiving a firing rod 60 that rotatingly engages firing components of the handle portion 22 (not shown). The firing rod 60 enters a proximal opening 62 along the longitudinal centerline of the frame ground 48. The distal portion of the frame ground 48 includes a firing bar slot 64 along its bottom that communicates with the proximal opening 62. A firing bar 66 longitudinally translates in the firing bar slot 64 and includes an upwardly projecting proximal pin 68 that engages a distal clevis end 70 of the firing rod 60.

The elongate shaft 16 supports the control of the bending articulation mechanism 14 by incorporating a rectangular reservoir cavity 72, one lateral portion depicted in a distal portion of the rotation knob 32. A bottom compartment 74 that resides within the rectangular reservoir cavity 72 has laterally spaced apart left and right baffles 76, 78. An articulation control actuator 80 slides laterally overtop of the bottom compartment 74, its downward laterally spaced left and right flanges 82, 84, which are outboard of the baffles 76, 78, each communicating laterally to left and right push buttons 86, 88 that extend outwardly from the respective shell halves of the rotation knob 32.

The lateral movement of the articulation control actuator 80 draws left and right flanges 82, 84 nearer and farther respectively to the left and right baffles 76, 78, operating against left and right reservoir bladders 90, 92 of a differential fluidic actuation system 94, each bladder 90, 92 communicating respectively and distally to left and right fluid conduits or passageways 96, 98 that in turn communicate respectively with left and right actuating bladders 100, 102. The latter differentially oppose and bend a distal portion of proximally grounded bending member, which is more particularly a proximally grounded T-bar 104 having a laterally flexible shaft 105 of the bending articulation mechanism 14.

The frame assembly 44 constrains these fluidic actuations and provides the proximal grounding to the T-bar 104 by including a top and distal recessed table 106 of the frame ground 48 upon which resides the fluid passages 96, 98 and actuating bladders 100, 102 on either side of the T-bar 104 whose proximal end is attached to a longitudinally aligned raised barrier rib 108 that also prevents inward expansion of the fluid passages 96, 98. The frame assembly 44 has a rounded top frame cover (spacer) 110 that slides overtop of the frame ground 48, preventing vertical expansion of the fluid passages 96, 98 and actuating bladders 100, 102. In particular, the frame cover 110 is part of an articulation locking member 111, described in greater detail below as part of an articulation locking mechanism 113.

A distal end ("rack") 112 of the T-bar 104 engages to pivot a proximally directed gear segment 115 of an articulating distal frame member 114 of the bending articulation mechanism 14. The articulating distal frame member 114 includes a distal firing bar slot 117 (FIG. 4) that guides the firing bar 66. An articulating closure ring 116 encompasses the articulating distal frame member 114 and includes a horseshoe aperture 118 that engages the anvil 42. A double pivoting attachment is formed between the closure straight tube 52 and articulating closure ring 116 over the bending articulation mechanism 14, allowing longitudinal closure motion even when the bending articulation mechanism 14 is articulated. In particular, top and bottom distally projecting pivot tabs 119, 120 on the closure straight tube 52 having pin holes 122, 124 respectively are longitudinally spaced away from corresponding top and bottom proximally projecting pivot tabs 126, 128 on the articulating closure ring 116 having pin holes 130, 132 respectively. An upper double pivot link 134 has longitudinally spaced upwardly directed distal and aft pins 136, 138 that engage pin holes 130, 122 respectively and a lower double pivot link 140 has longitudinally spaced downwardly projecting distal and aft pins 142, 144 that engage pin holes 132, 124 respectively.

The frame ground 48 pivots around a single pin, depicted as the pivot pin 145 that joins frame ground 48 to distal frame member 114. With the anvil 42 open, the pivot pin 145 of frame ground 48 is aligned with the distal most position of upper and lower double pivot links 134, 140 of the closure sleeve assembly 46. This positioning allows easy pivoting and rotation of the staple applying assembly 20 while the anvil 42 is open. When the closure sleeve assembly 46 is moved distally to pivot anvil 42 closed, the closure straight tube 52 moves distally about frame ground 48 and the articulated closure ring 116 moves distally along the articulating distal frame member 114 axis as urged by pivot links 134, 140. Dual pivoting pins 136, 138 and 142, 144 on links 134, 140 facilitate engagement with closure straight tube 52 and articulated closure ring 116 as they are urged towards the distal closure position when the device is articulated (not shown). At the distal closure position, the frame ground pivot pin 145 is vertically aligned with proximal pivot pins 138, 144 at full articulation or may fall at any point between distal pins 136, 142 and proximal pins 138, 144 while working effectively.

Figure 4:
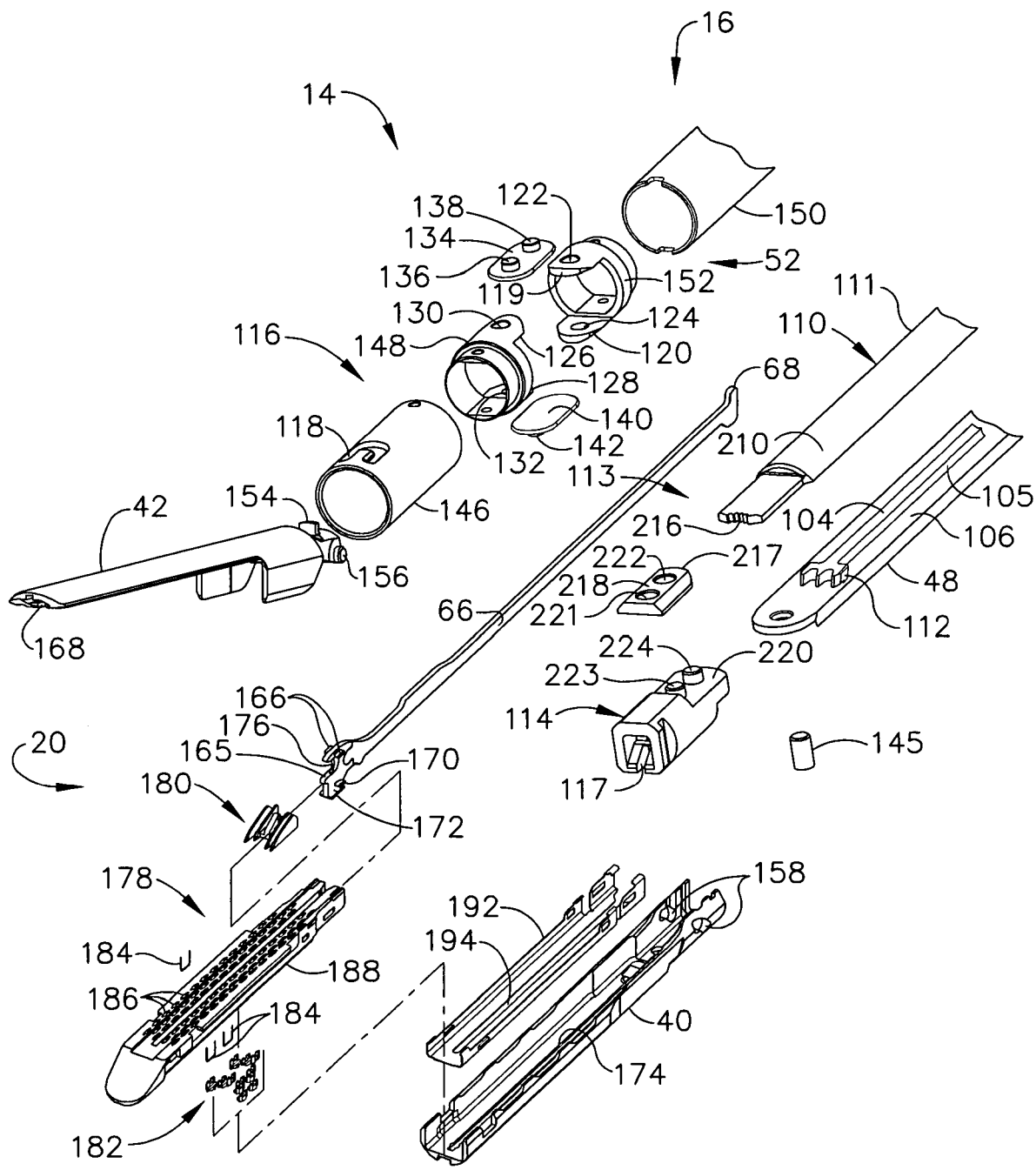
FIG. 4 is a left front perspective disassembled view of distal portions of an implement portion of the surgical stapling and severing instrument of FIG. 1, including the staple applying assembly and articulation mechanism.

With particular reference to FIG. 4, the articulating closure ring 116 is shown for enhanced manufacturability to include a short tube 146 attached to an articulating attachment collar 148 that includes the proximally projecting pivot tabs 126, 128. Similarly, the straight closure tube 52 is assembled from a long closure tube 150 that attaches to an aft attachment collar 152 that includes the distally projecting pivot tabs 119, 120. The horseshoe aperture 118 in the short closure tube 146 engages an upwardly projecting anvil feature 154 slightly proximal to lateral pivot pins 156 that engage pivot recesses 158 inside of the elongate staple channel 40.

With reference to FIGS. 4, 4A, 4B, and 5, the firing bar 66 distally terminates in an E-beam 165 that includes upper guide pins 166 that enter an anvil slot 168 in the anvil 42 to verify and assist in maintaining the anvil 42 in a closed state during staple formation and severing. Spacing between the elongate staple channel 40 and anvil 42 is further maintained by the E-beam 165 by having middle pins 170 slide along the top surface of the elongate staple channel 40 while a bottom foot 172 opposingly slides along the undersurface of the elongate staple channel 40, guided by a longitudinal opening 174 in the elongate staple channel 40. A distally presented cutting surface 176 of the E-beam 165, which is between the upper guide pins 166 and middle pin 170, severs clamped tissue while the E-beam 165 actuates a replaceable staple cartridge 178 by distally moving a wedge sled 180 that causes staple drivers 182 to cam upwardly driving staples 184 out of upwardly open staple holes 186 in a staple cartridge body 188, forming against a staple forming undersurface 190 of the anvil 42. A staple cartridge tray 192 encompasses from the bottom the other components of the staple cartridge 178 to hold them in place. The staple cartridge tray 192 includes a rearwardly open slot 194 that overlies the longitudinal opening 174 in the elongate staple channel 40, thus the middle pins 170 pass inside of the staple cartridge tray 192.

Figure 4A:
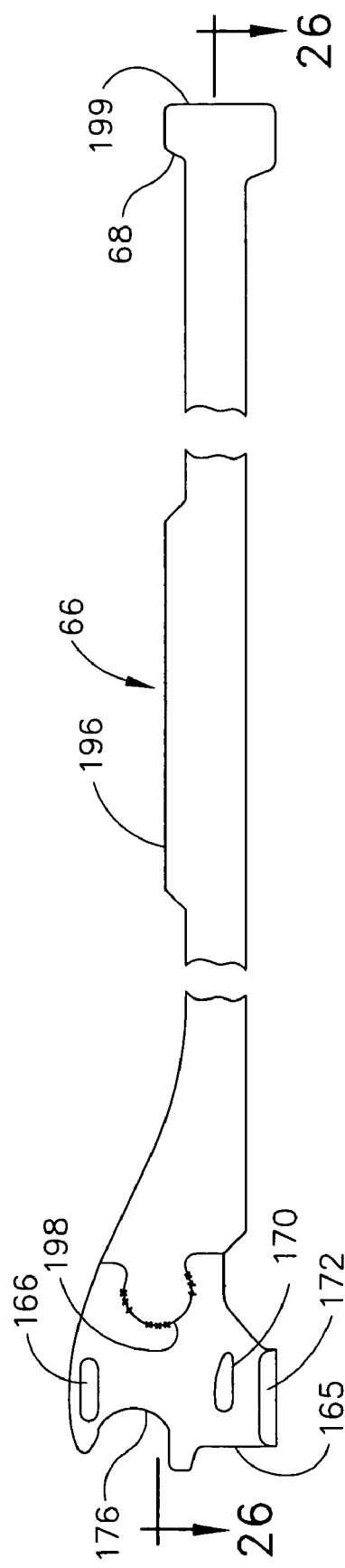
FIG. 4A is a left side view of a firing bar of the implement portion of the surgical stapling and severing instrument of FIG. 4.
Figure 4B:
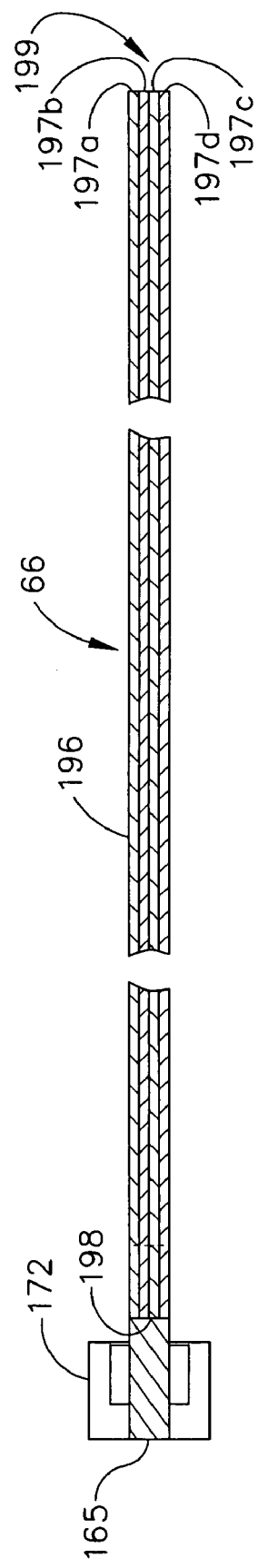
FIG. 4B is a top view of the firing bar of FIG. 4A taken in horizontal cross section along lines 26-26.
Figure 5:
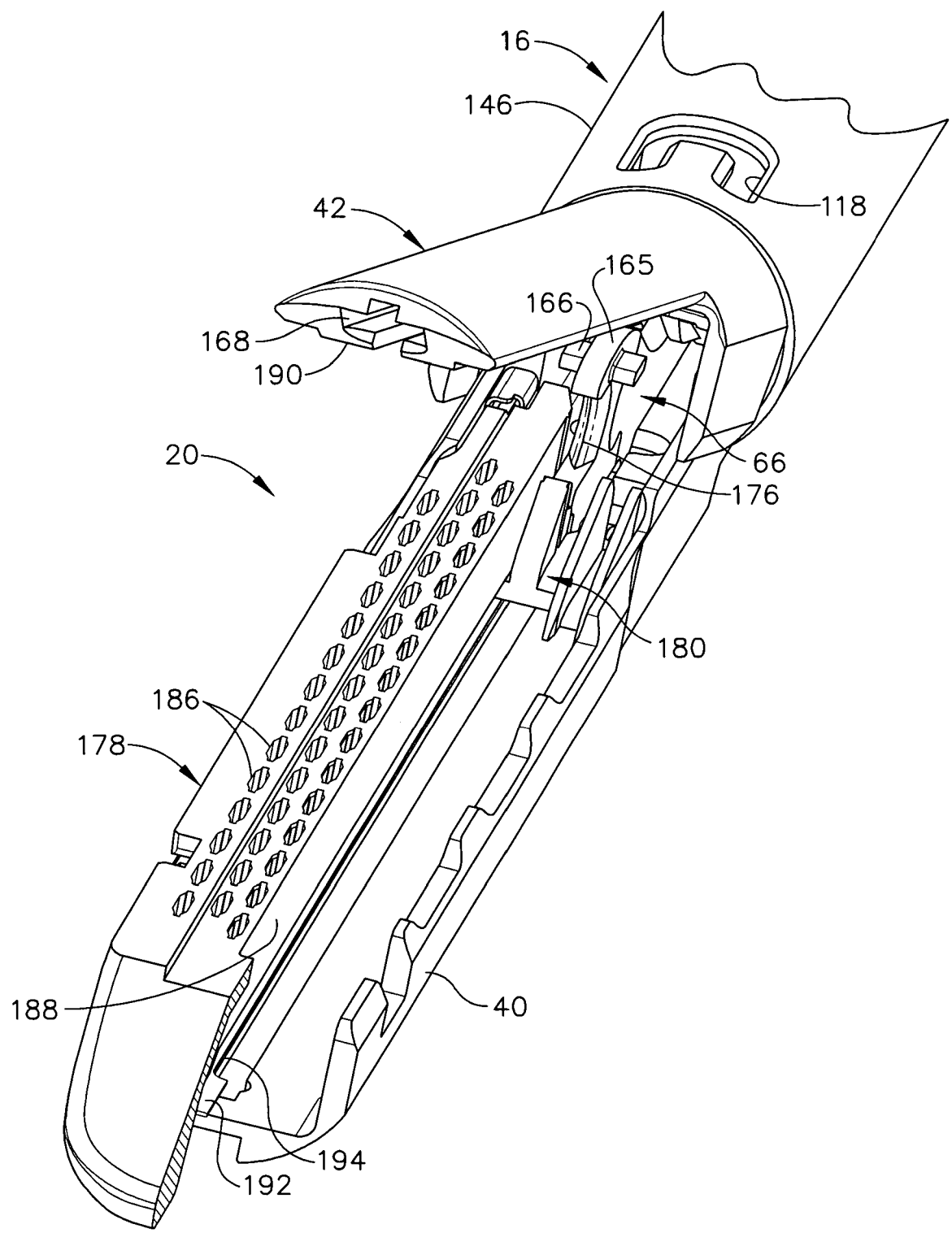
FIG. 5 is a top perspective view of the staple applying assembly of FIGS. 1 and 4 with a lateral half of a staple cartridge removed to expose components driven by a firing motion.
Figure 6:
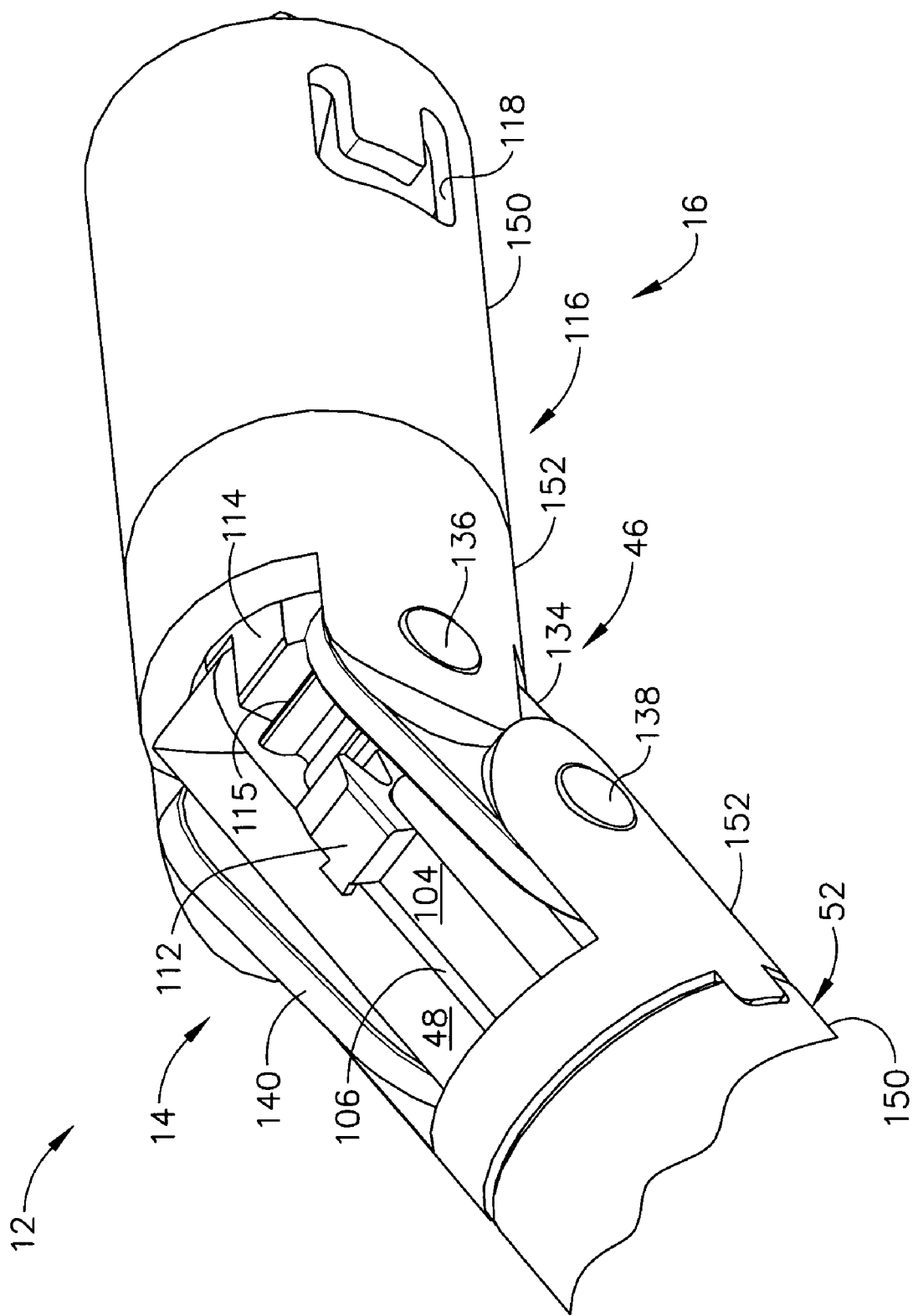
FIG. 6 is perspective detail view of an articulation joint of the surgical stapling and severing instrument of FIG. 1 depicting a double pivoting closure sleeve assembly at a proximal position with a single pivot frame ground incorporating a bending articulation mechanism.
Figure 7:
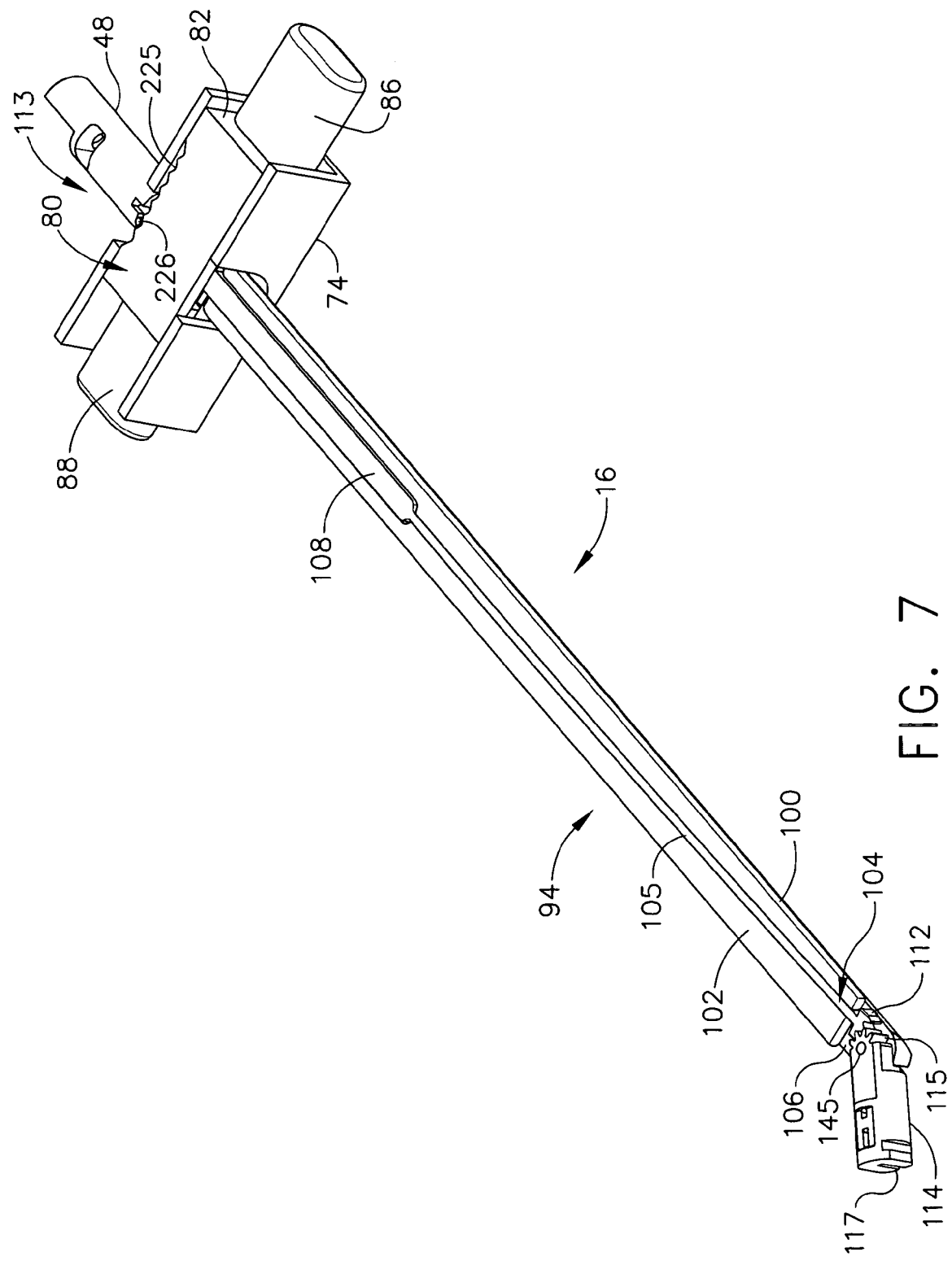
FIG. 7 is a front perspective view of an implement portion of the surgical instrument of FIG. 1 with a double pivot closure sleeve assembly and end effector removed to expose a single pivot frame ground articulated by a first version of a bending articulation mechanism including differential fluidic actuation.
Figure 10:
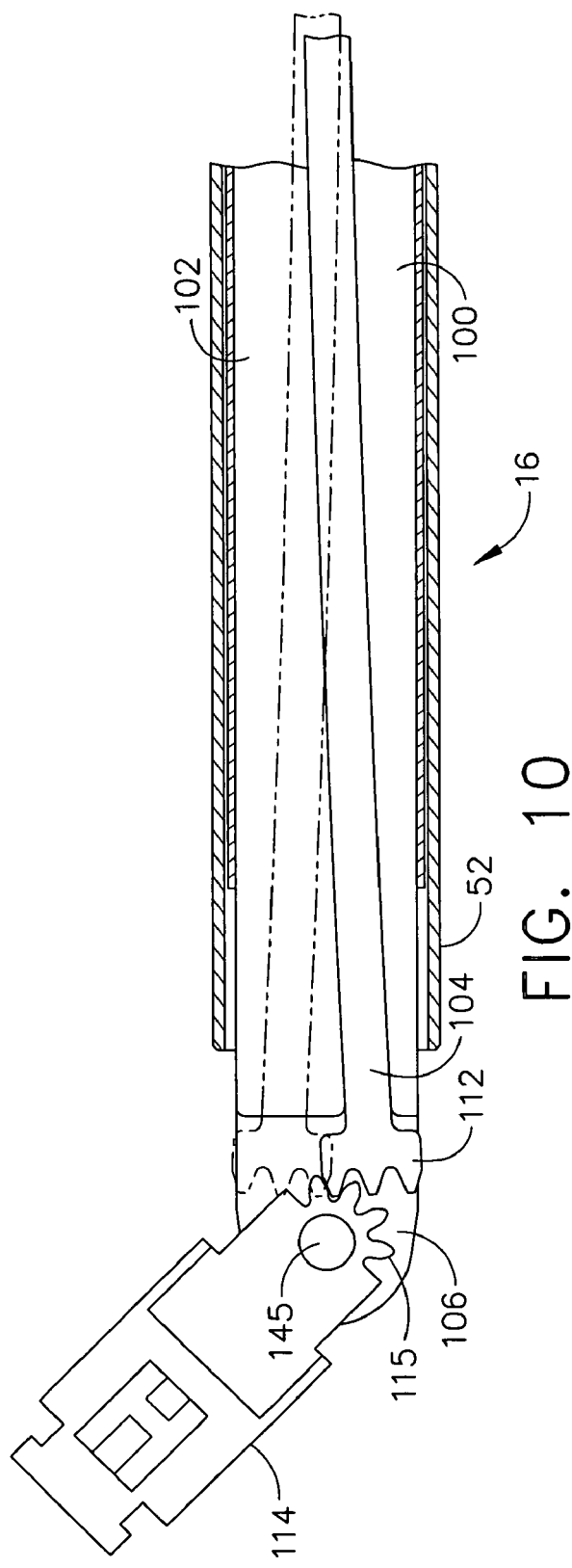
FIG. 10 is top detail view of a distal portion of the bending articulation mechanism of FIG. 7 bent to articulate to the right with a leftward articulation depicted in phantom.

With particular reference to FIGS. 4A-4B, the firing bar 66 advantageously includes a proximal laminated portion 196 having a plurality of identical thin strips 197a-197d. A male end 198 of the proximal laminated portion 196 is formed by welding a distal bulbous cutout shape of each identical thin strip 197a-197d to each other and to a corresponding proximal recess 199 formed in the E-beam 165. The identical thin strips 197a-197d facilitate lateral articulation of the implement portion 12 by longitudinally sliding against each other when bent to accommodate the bending radius, thus presenting a significantly lower force to articulate the proximal laminated portion 196 than a solid firing bar of comparable thickness and strength.

The staple applying assembly 20 is described in greater detail in co-pending and commonly-owned U.S. patent application Ser. No. 10/955,042, "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

In FIGS. 3-4, and 7-9, the articulation locking mechanism 113 is advantageously incorporated to maintain the staple applying assembly 20 at a desired articulation angle. The articulation locking mechanism 113 reduces loads on the left and right actuating bladders 100, 102. In particular, a compression spring 202 (FIG. 3) is proximally positioned between a proximal end 204 of the articulation locking member 111 and the handle portion 22, biasing the articulation locking member 111 distally.

With particular reference to FIG. 4, selective abutting engagement of a distal frictional surface, depicted as a toothed recess 216 distally projecting from the articulation locking member 111 is engaged to a corresponding locking gear segment 217 in a brake plate 218 received into a top proximal recess 220 of the articulating frame member 114. Distal and proximal holes 221, 222 in the brake plate 218 receive distal and proximal pins 223, 224 that upwardly project from the top proximal recess 220.

With particular reference to FIGS. 3 and 7-10, articulation control actuator 80 is laterally moved to compress one of the left and right proximal reservoir bladders 90, 92 and thereby expands the corresponding one of the distal left and right actuation bladders 100, 102, bending the T-bar 104 to the opposite side. Thus, lateral movement of the articulation control actuator 80 articulates the distal frame 114 clockwise about the single pivot frame ground 48 for a leftward bending T-bar 104 and vice versa. The articulation control actuator 80 advantageously also automatically engages and disengages the articulation locking mechanism 113. In particular, a toothed detent surface 225 along a proximal top surface of the articulation control actuator 80 receives an upwardly projecting locking pin 226 from the proximal end 204 of the articulation locking member 111. The engagement of the locking pin 226 within the root of the toothed detent surface 225 provides sufficient distal movement of the articulation locking member 111 for locking engagement of the locking gear segment 217 in the brake plate 218. Lateral movement by an operator of the compression member 272 proximally urges the locking pin 226 proximally, and thus disengages the articulation locking member 111 from the brake plate 218. When the operator releases the articulation control actuator 80, the locking pin 226 is urged by the compression spring 202 into the adjacent detent in detent surface 225 to lock the locking mechanism 111, and thereby the staple applying assembly 20, constrains the bending articulation mechanism 14 at a desired articulation position by constraining and expanding the inflated shape of the proximal left and right reservoir bladders 90, 92.

Figure 11:
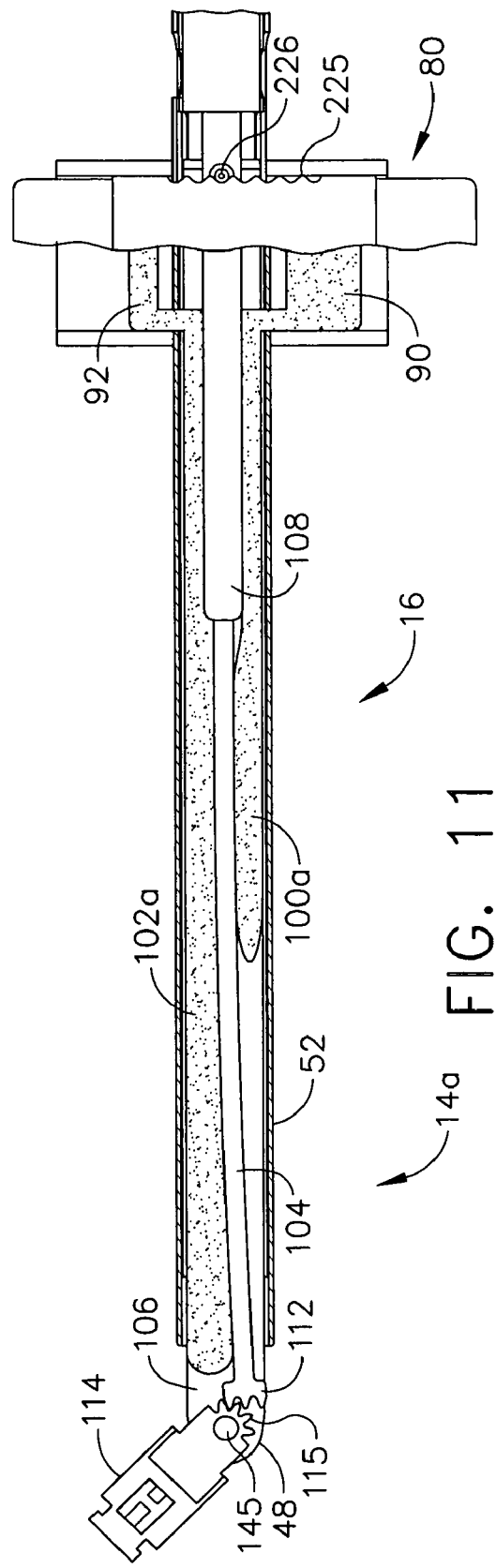
FIG. 11 is a top view of a second version of a bending articulation mechanism with longitudinally expansive, differential actuating fluidic bladders for the surgical stapling and severing instrument of FIG. 1.

In FIG. 11, a second version of a bending articulation mechanism 14a for the surgical stapling and severing instrument 10 includes longitudinally expansive, differential left and right actuating fluidic bladders 100a, 102a of a differential fluidic actuation system 94a.

Figure 14:
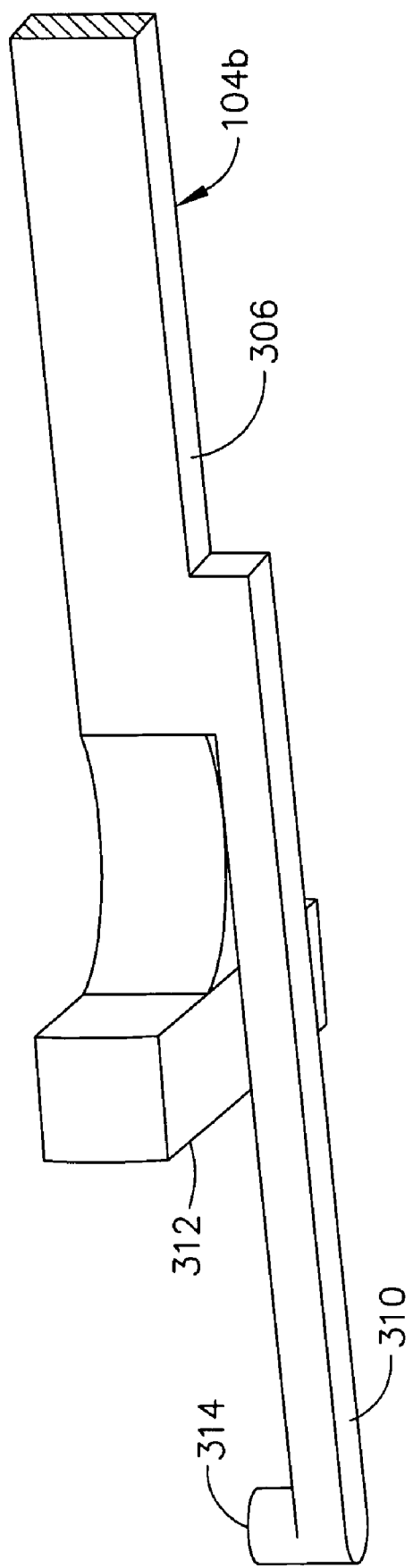
FIG. 14 is a lower perspective detail view of a distal end of the compound bending member of FIGS. 12-13.

In FIGS. 12-14, a third version of a bending articulation mechanism 14b for the surgical stapling and severing instrument 10 includes a compound bending member ("tiller") 104b whose proximal end 300 is laterally moved to effect articulation control. The compound bending member 104b is constrained to move laterally within an elongate shaft 16b. The proximal end 300 is aft of a proximal aperture 302 in the elongate shaft 16b that causes lateral movement of the proximal end 300 to laterally deflect a rigidly extended proximal leg portion 304 toward an opposite side of the elongate shaft 16b. A distal leg portion 306 of the compound bending member 104b flexibly attached to the proximal leg portion 304 at a knee 308 is also flexibly attached near a distal end 310 to a sliding lateral cross member 312 that constrains the distal end 310 to move in a shallow lateral arc. The distal end 310 includes a pivot pin 314 that resides within a radial slot 316 formed in a round camming extension 320 attached to a articulating distal frame ground 114b aft of a pivotal attachment 322 between the articulating distal frame ground 114b and a proximal frame ground 48b of the elongate shaft 16b.

Thus with a rightward movement of the proximal portion 300 of the compound bending member 104b, the knee 308 is moved to the left within the proximal frame ground 48b, angling the distal leg portion 306 such that the distal end 310 is offset to the right in front of the sliding lateral cross member 312, causing the pivot pin 314 to move the radial slot 316 counterclockwise when viewed from above thereby moving the distal frame ground 114b to the left. The corresponding opposite movement is achieved with a leftward movement of the proximal portion 300.

Figure 15:
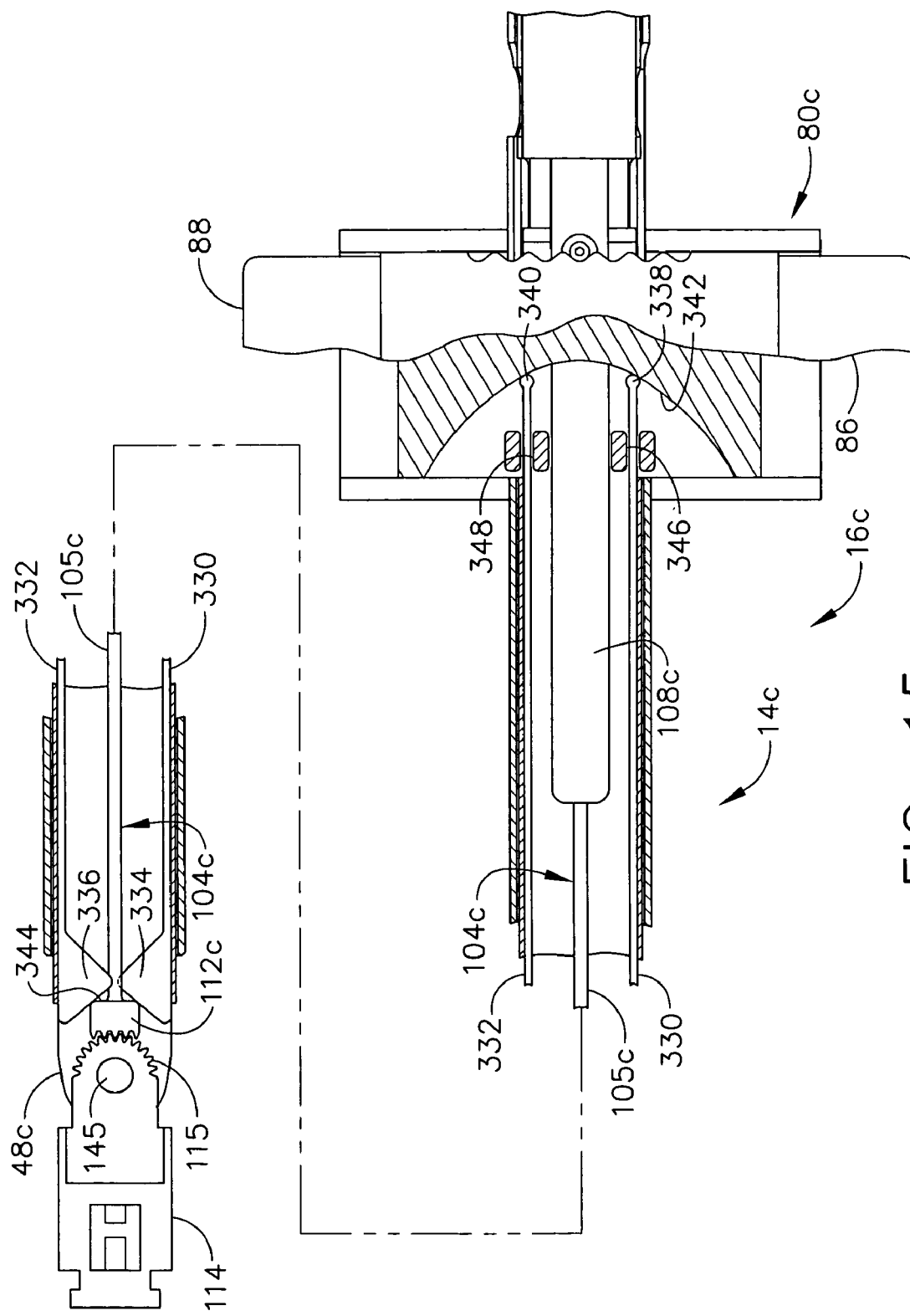
FIG. 15 is a top view of an elongate shaft partially cut away having a fourth version of a bending articulation mechanism including differential cam bars for the surgical stapling and severing instrument of FIG. 1.
Figure 16:
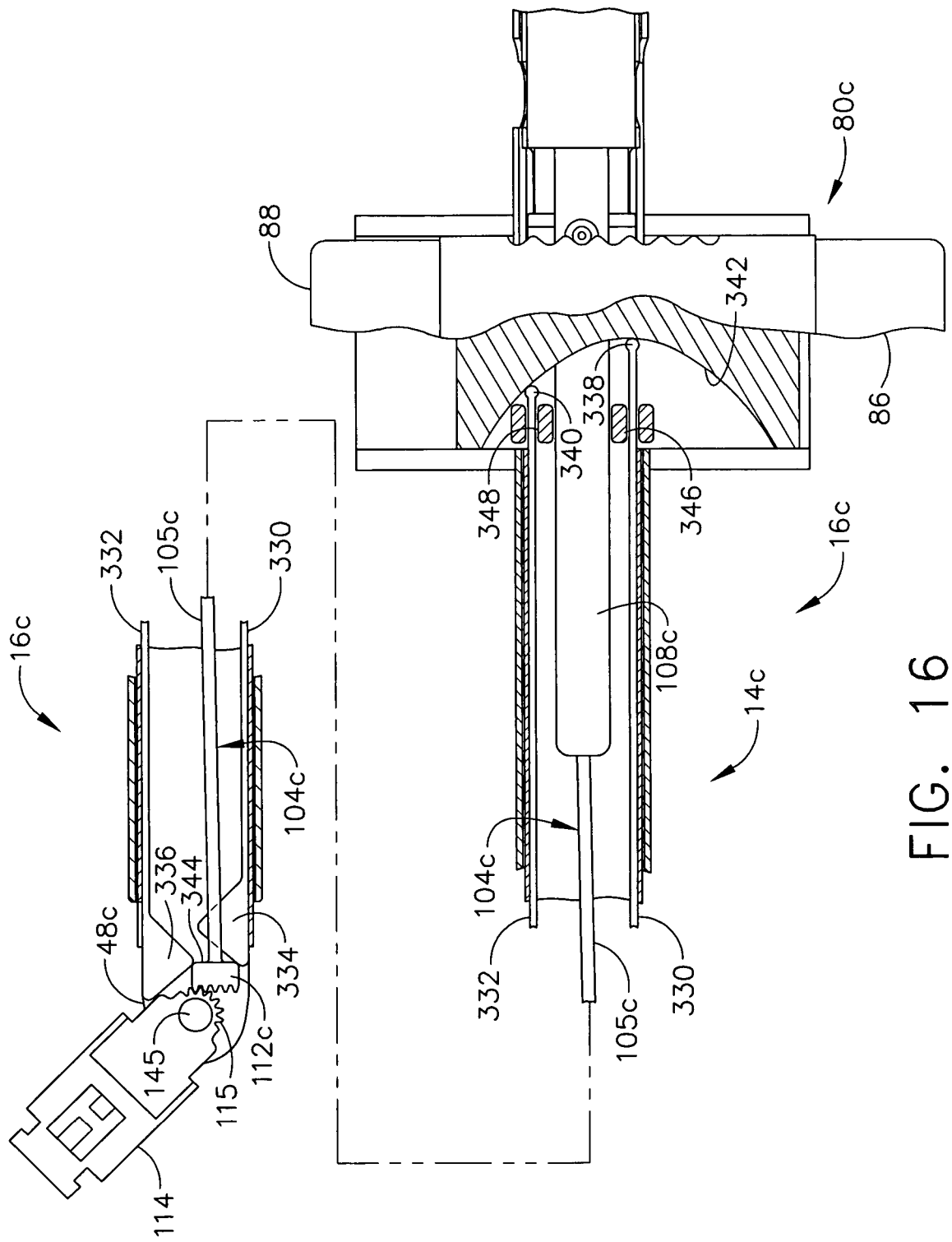
FIG. 16 is a top view of the elongate shaft partially cut away having the fourth version of the bending articulation mechanism including the differential cam bar of FIG. 15 in an articulated state.

In FIGS. 15-16, a fourth version of a bending articulation mechanism 14c for the surgical stapling and severing instrument of FIG. 1 includes left and right differential cam bars 330, 332 that cam against opposite lateral corners of a vertically enlarged rack 112c of a bending member T-bar 104c. Thus, a bending shaft 105c and both of left and right inwardly directing camming surfaces 334, 336 of respective left and right differential cam bars 330, 332 are vertically deconflicted from one another. Moreover, the camming surfaces 334, 336 may be vertically deconflicted from each other to allow for a laterally narrower elongate shaft 16c. It should be appreciated that a raised barrier rib 108c that serves as the proximal ground for the bending shaft 105c of the T-bar 104c is proximally grounded to a frame ground 48c.

An articulation control actuator 80c differentially longitudinally moves proximal round ends 338, 340 respectively of the left and right differential cam bars 330, 332. When either the left or right push buttons 86, 88 are depressed, an interposed distally projecting recessed camming surface 342 abuts the proximal round ends 338, 340, working in opposition with a proximal camming surface 344 of the vertically enlarged rack 112c that abuts the distally angled surfaces of the left and right inwardly directed camming surfaces 334, 336 of the differential cam bars 330, 332. Insofar as the length of the bending shaft 105c is fixed, distal movement of a selected cam bar 330, 332 cams the rack 112c toward the opposite lateral side, allowed by a proximally retreating unselected cam bar 332, 330. Left and right guide slots 346, 348 formed in a lower base 74c of the articulation control actuator 80c constrains the proximal round ends 338, 340 to move longitudinally.

Figure 17:
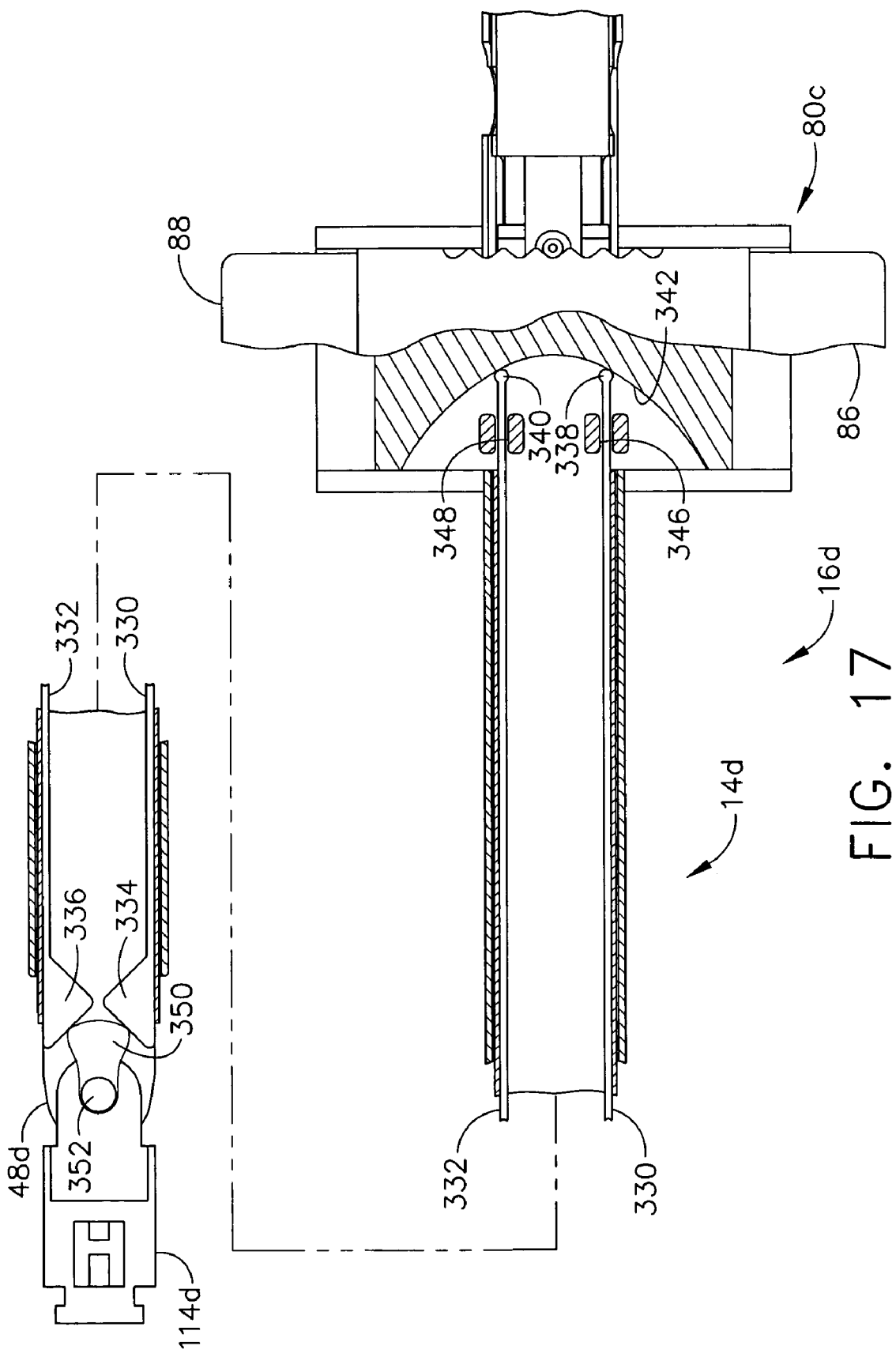
FIG. 17 is a top view of an elongate shaft partially cut away having a fifth version of a bending articulation mechanism for the surgical stapling and severing instrument of FIG. 1.
Figure 18:
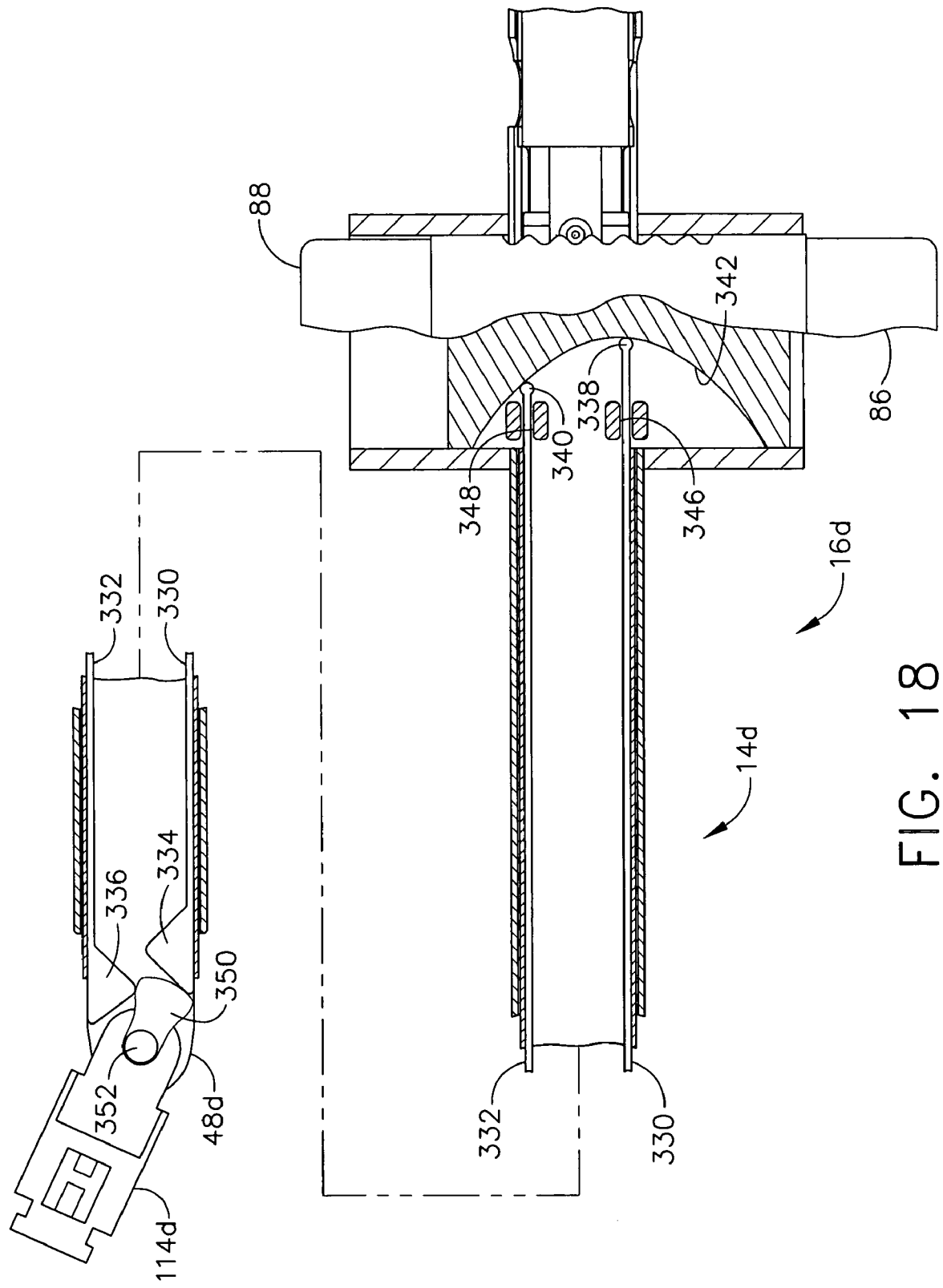
FIG. 18 is a top view of the elongate shaft partially cut away having the fifth version of the bending articulation mechanism of FIG. 17 in an articulated state.

In FIGS. 17-18, a fifth version of a bending articulation mechanism 14d for the surgical stapling and severing instrument 10 of FIG. 1 is as described for FIGS. 15-16 but with the T-bar 104c omitted. Instead, the differential cam bars 330, 332 act against opposite rounded proximal corners of a proximal camming extension 350 attached to a articulating distal frame ground 114b aft of a pivotal attachment 352 between an articulating distal frame ground 114d and a proximal frame ground 48d of the elongate shaft 16d.

Figure 19:
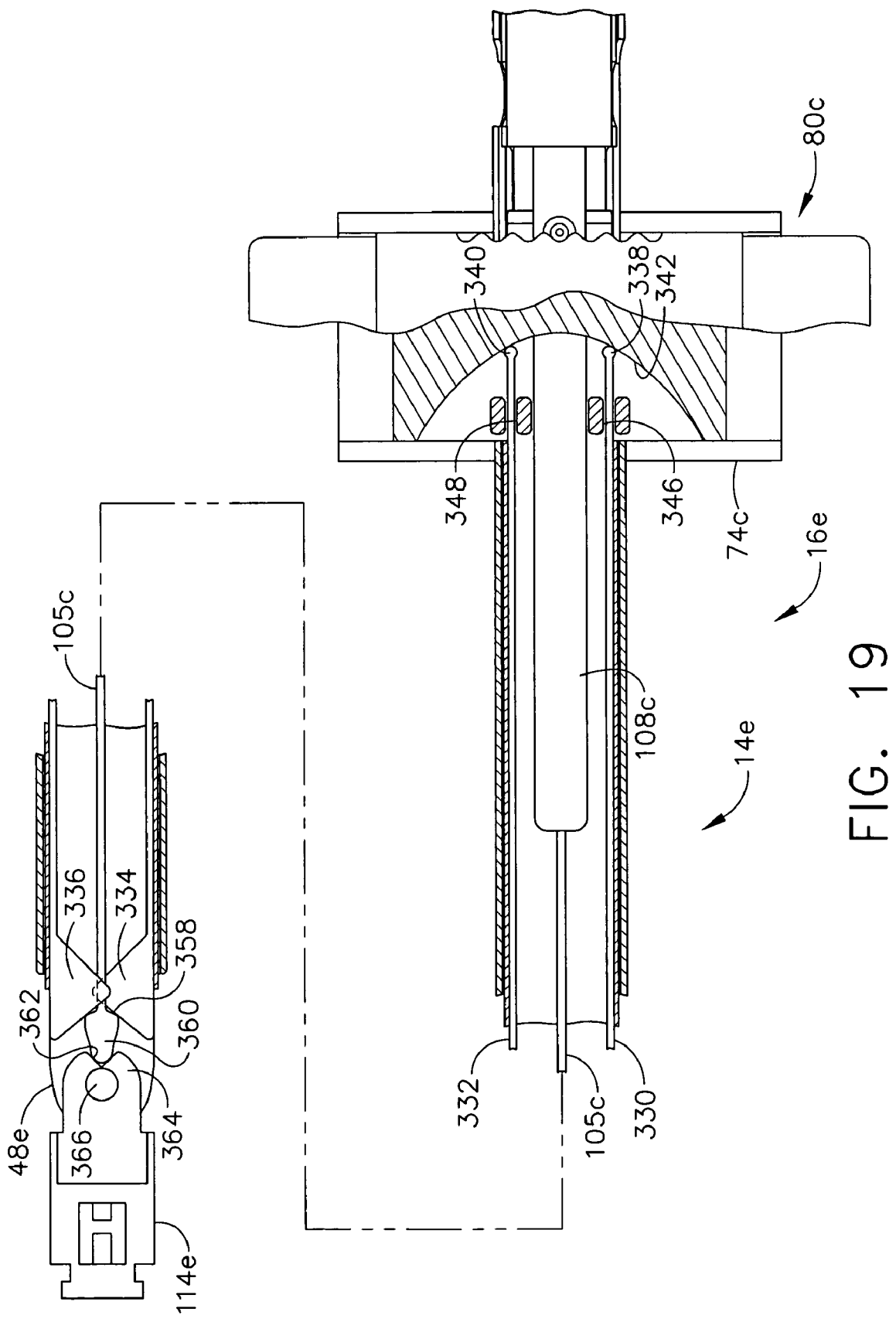
FIG. 19 is a top view of an elongate shaft partially cut away having a sixth version of a bending articulation mechanism for the surgical stapling and severing instrument of FIG. 1.
Figure 20:
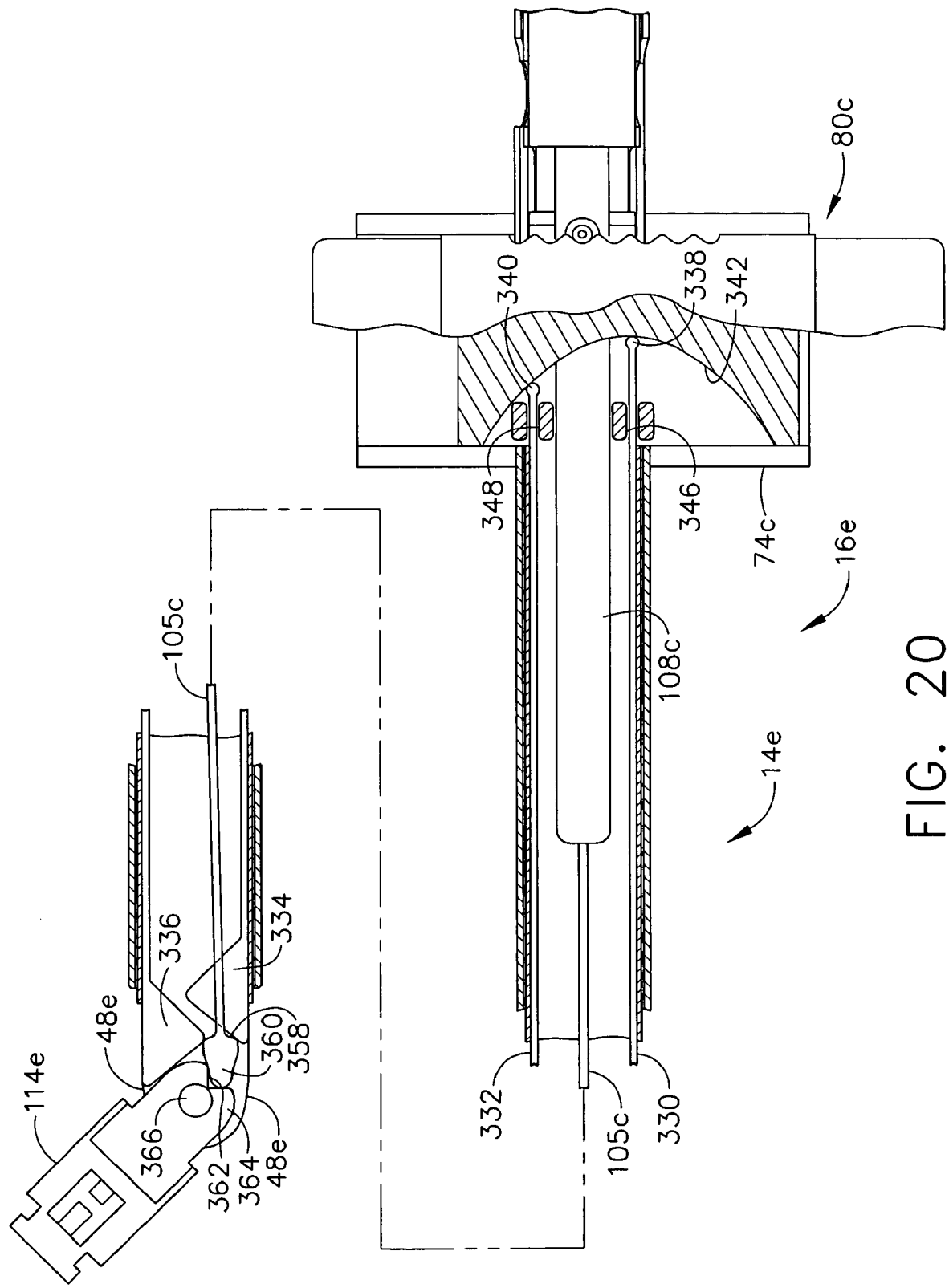
FIG. 20 is a top view of the elongate shaft partially cut away having the sixth version of the bending articulation mechanism of FIG. 19 in an articulated state.

In FIGS. 19-20, a sixth version of a bending articulation mechanism 14d for the surgical stapling and severing instrument 10 of FIG. 1 is as described for FIGS. 15-16 an alternative engagement between a distal frame ground 114e and a vertically enlarged cam point 112e of a bending member 104e that retains a proximal camming surface 358 upon which the differential cam bars 330, 332 act. Instead of a toothed rack, the vertically enlarged cam point 112e distally presents a rounded tip 360 that resides within a proximally directed cam recess 362 formed into a round proximal extension 364 attached to an articulating distal frame ground 114e aft of a pivotal attachment 366 between the articulating distal frame ground 114e and a proximal frame ground 48e of the elongate shaft 16e.

Figure 21:
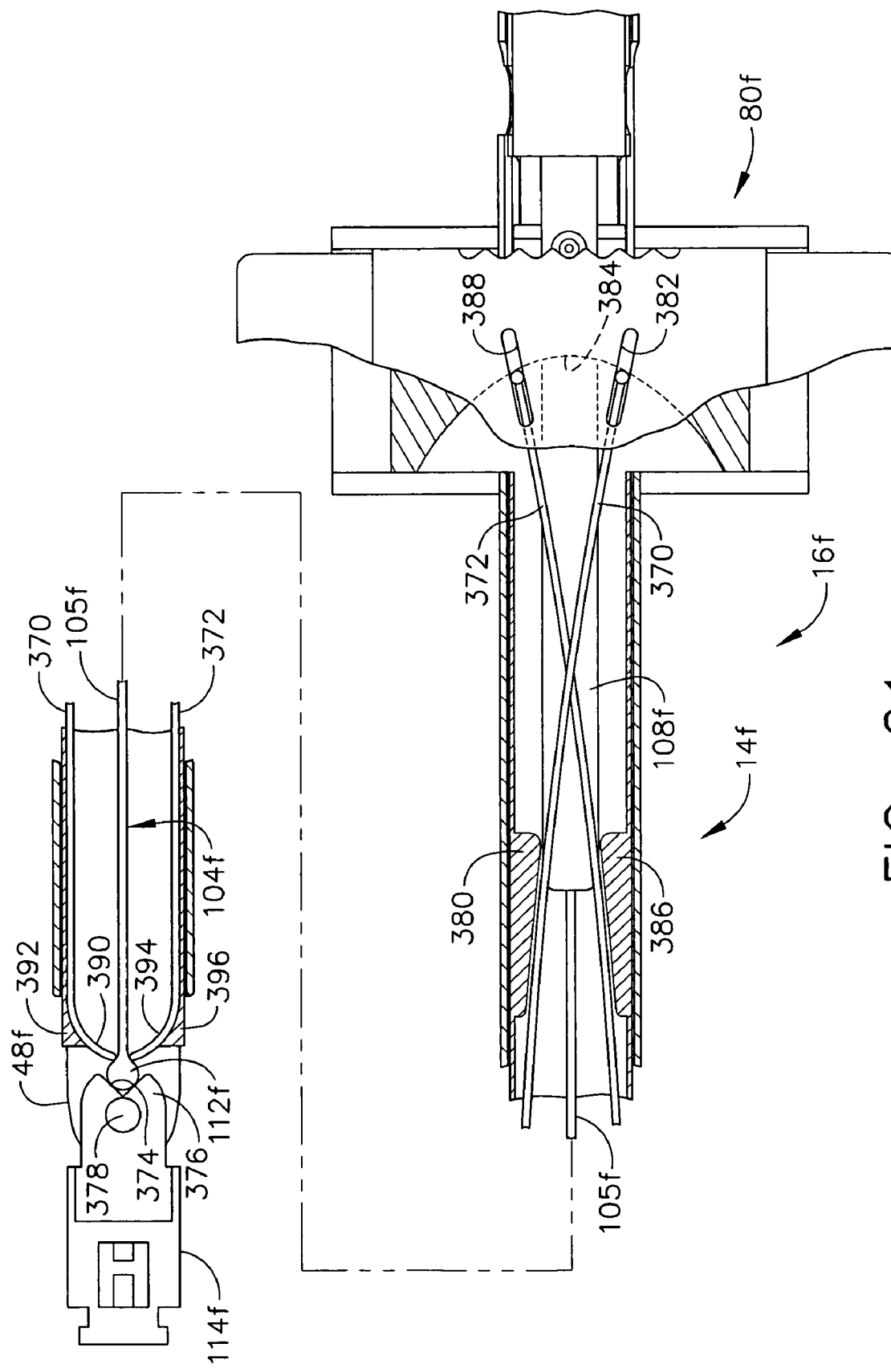
FIG. 21 is a top view of an elongate shaft partially cut away having a seventh version of a bending articulation mechanism for the surgical stapling and severing instrument of FIG. 1.
Figure 22:
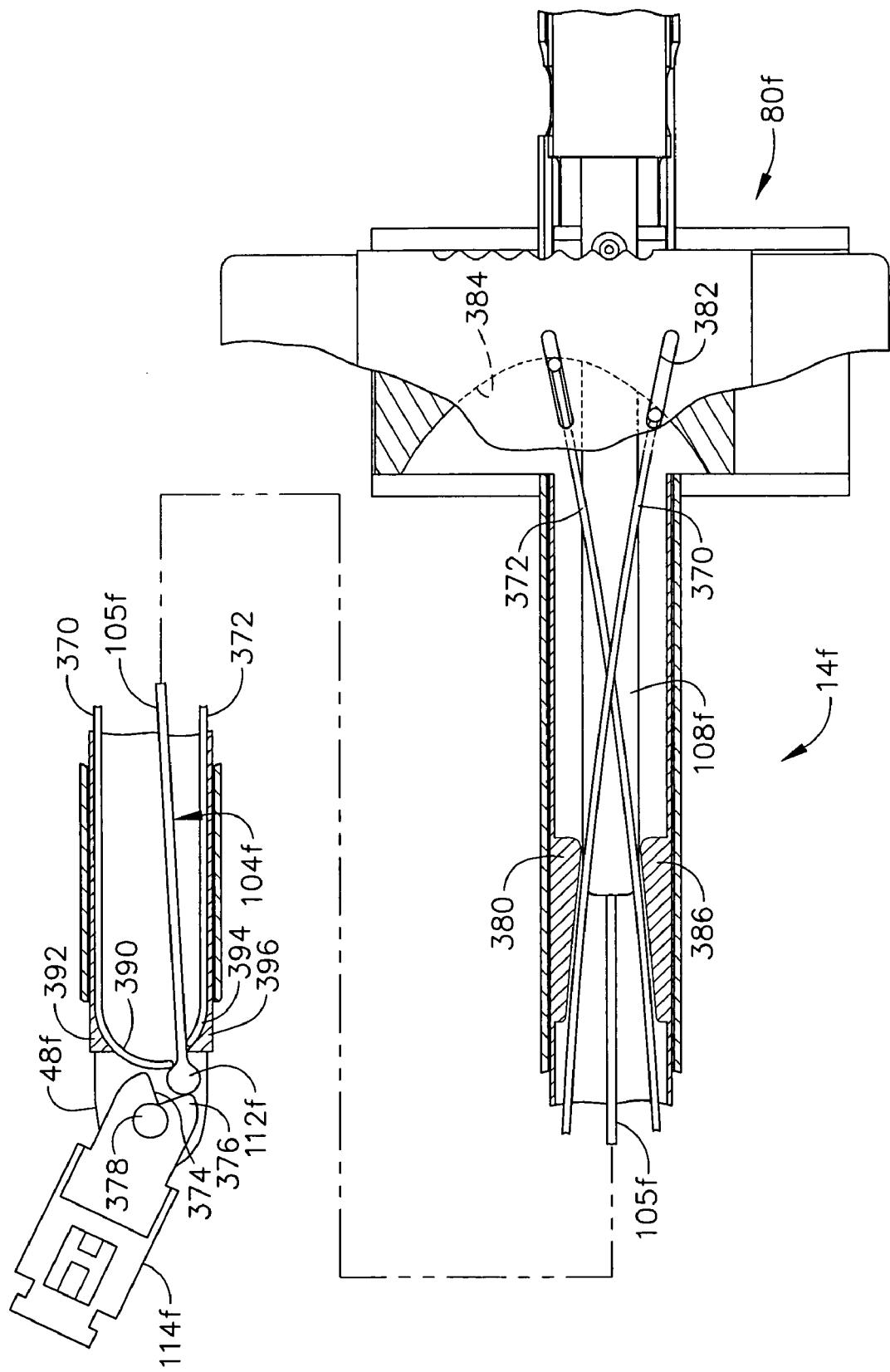
FIG. 22 is a top view of the elongate shaft partially cut away having the seventh version of the bending articulation mechanism of FIG. 21 in an articulated state.

In FIGS. 21-22, a seventh version of a bending articulation mechanism 14f for the surgical stapling and severing instrument of FIG. 1 includes first and second crossed, differentially, longitudinally translating flexible push rods 370, 372 that act against a bending member 104f having a round distal end 112f attached to a flexible shaft 105f that is proximally grounded by a raised barrier rib 108f to a proximal frame ground 48f. Instead of a toothed rack, the round distal end 112f resides within a proximally directed cam recess 374 formed into a round proximal extension 376 attached to an articulating distal frame ground 114f aft of a pivotal attachment 378 between the articulating distal frame ground 114f and the proximal frame ground 48f of the elongate shaft 16f.

The elongate shaft 16f includes a right proximal outer guide 380 that directs the first push rod 370 from the right side to the left side of the elongate shaft 16f to attach within a left sliding attachment 382 attached to a distally directed camming recess 384 in an articulation control actuator 80f. The elongate shaft 16f includes a left proximal outer guide 386 that directs the second push rod 372 from the right side to the left side of the elongate shaft 16f crossing under the first push rod 370 to attach within a right sliding attachment 388 attached to the distally directed camming recess 386 in the articulation control actuator 80*f*. A distal end 390 of the first push rod 370 is curved by a right curved guide 392 inwardly to abut a proximal right side of the attachment between the flexible shaft 105*f* and the round distal end 112*f* of the bending member 104*f*. Similarly, a distal end 394 of the second push rod 372 is curved by left curved guide 396 inwardly to abut a proximal left side of the attachment between the flexible shaft 105*f* and the round distal end 112*f* of the bending member 104*f*.

Figure 23:
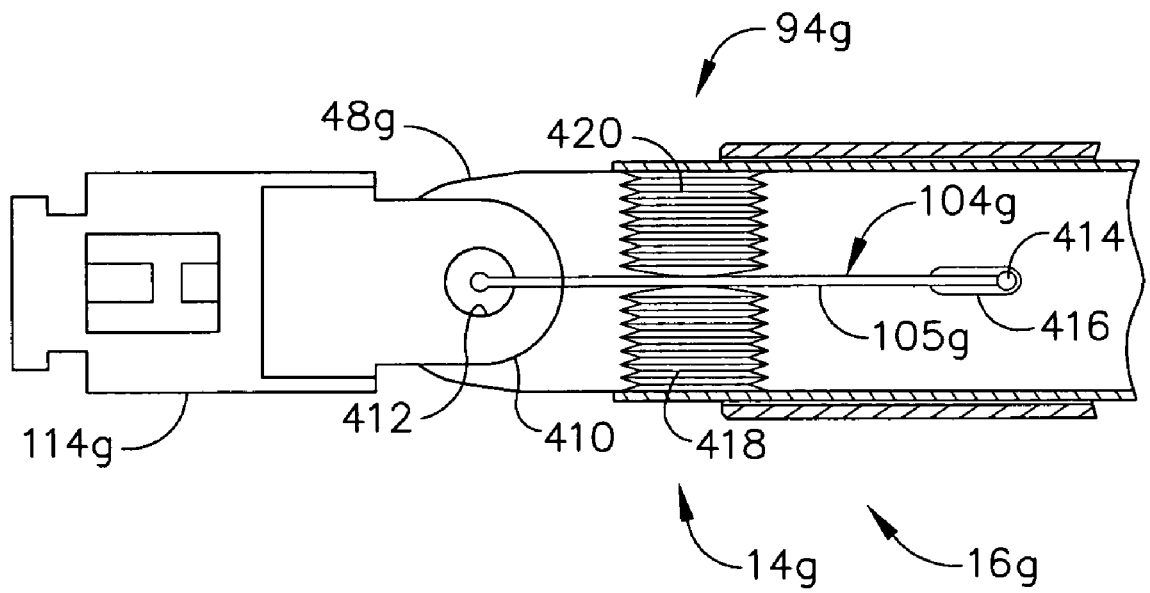
FIG. 23 is a top view of an elongate shaft partially cut away having an eighth version of a bending articulation mechanism for the surgical stapling and severing instrument of FIG. 1.
Figure 24:
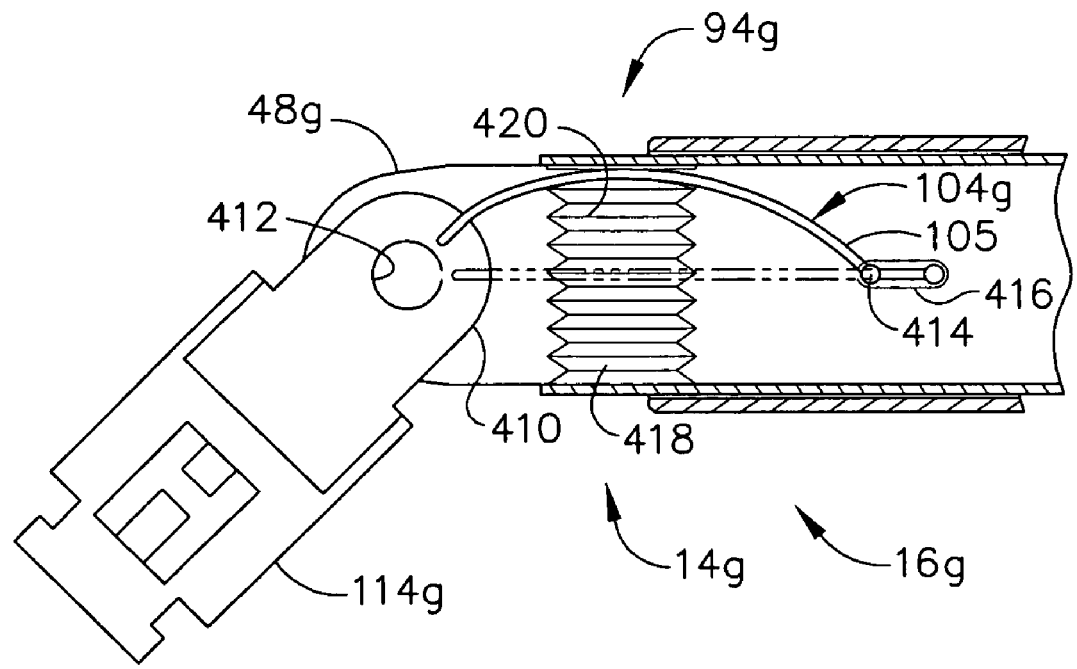
FIG. 24 is a top view of the elongate shaft partially cut away having the eighth version of the bending articulation mechanism of FIG. 23 in an articulated state.

In FIGS. 23-24, a seventh version of a bending articulation mechanism 14*g* for the surgical stapling and severing instrument 10 of FIG. 1 has a bending member 104*g* that is proximally extending from a round proximal extension 410 attached to an articulating distal frame ground 114*f* aft of a pivotal attachment 412 between the articulating distal frame ground 114*g* and a proximal frame ground 48*g* of the elongate shaft 16*g*. A proximal end of the bending shaft 105*g* of the bending member 104*g* terminates in a proximal pin 414 that slides within a longitudinal slide attachment 416 formed along a centerline of the proximal frame ground 48*g*. Left and right lateral bellows 418, 420 contacting opposite lateral sides of the bending shaft 105*g* are differentially and laterally expanded/contracted to bend the bending member 104*g* and thereby pivot the distal frame ground 114*g*. The lateral bellows 418, 420 are part of a differential fluidic actuation system 94*g*.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

It will be appreciated that the terms "proximal" and "distal" are used herein with reference to a clinician gripping a handle of an instrument. Thus, the surgical stapling assembly 20 is distal with respect to the more proximal handle portion 22. It will be further appreciated that for convenience and clarity, spatial terms such as "vertical" and "horizontal" are used herein with respect to the drawings. However, surgical instruments are used in many orientations and positions, and these terms are not intended to be limiting and absolute.

What is claimed is:

1. A surgical instrument, comprising:
an end effector including a proximal camming surface;
an elongate shaft including a hollow chamber and a frame aligned with a longitudinal axis of the elongate shaft;
an articulation joint pivotally attaching the end effector to a distal end of the elongate shaft;
a bending member comprising a cantilever beam positioned within the hollow chamber of the shaft and bendable therein, the bending member extending along the longitudinal axis and having a proximal end attached to the elongate shaft and a distal end engaged to the proximal camming surface of the end effector; and
an articulation control actuator proximally attached to the elongate shaft and comprising a first differential fluidic actuation system operably configured to longitudinally transfer fluid from a first fluid actuator of the articulation control actuator to a second fluid actuator positioned adjacent to the bending member, wherein the longitudinal fluid transfer bends the bending member to laterally to deflect the distal end of the bending member in a direction away from the longitudinal axis to articulate the end effector.

2. The surgical instrument of claim 1, wherein the distal end of the bending member comprises a rack, the proximal camming surface of the end effector comprising a gear segment.

3. The surgical instrument of claim 1, wherein the articulation control actuator further comprises a second differential fluidic actuation system longitudinally parallel to the first differential fluidic actuation system, wherein the second differential fluidic actuation system comprises a third fluid actuator of the articulation control actuator and a fourth fluid actuator positioned laterally adjacent to the bending member, the second differential fluidic actuation system configured to longitudinally transfer fluid from the third fluid actuator to the fourth fluid actuator in response to selective actuation of the articulation control actuator to selectively articulate the end effector, wherein the second and fourth fluid actuators further comprises a pair of actuating bladders opposingly positioned on opposite lateral sides of the bending member and substantially encompassed by the elongate shaft.

4. The surgical instrument of claim 3, wherein each actuating bladder is operably configured to laterally expand in response to received fluid.

5. The surgical instrument of claim 4, wherein each actuating bladder is operably configured to longitudinally expand in response to received fluid.

6. The surgical instrument of claim 3 wherein the first and third actuators of the longitudinally parallel first and second differential fluidic actuation systems further comprises fluid reservoirs opposingly positioned on opposite lateral sides of the articulation control actuator and each fluid reservoir communicates fluid with a longitudinally associated actuator bladder on a same lateral side of the surgical instrument in response to actuation of the articulation control actuator.

7. The surgical instrument of claim 6 further comprising fluid passageways for communicating fluids therein between the fluid reservoirs and the actuator bladders.

8. The surgical instrument of claim 3 wherein the articulation control actuator moves laterally to articulate the end effector.

9. The surgical instrument of claim 8 wherein when the articulation control actuator moves laterally from a first lateral side toward a second lateral side, a distal tip of the end effector articulates toward the first lateral side.

10. The surgical instrument of claim 1 further comprising a locking member to lockingly engage with the end effector when the articulation control actuator is unactuated.

11. The surgical instrument of claim 10 further comprising a locking member to unlock the end effector when the articulation control actuator is actuated to articulate the end effector.

12. The surgical instrument of claim 10 wherein the locking member moves longitudinally to lock the end effector.

13. A surgical instrument, comprising:
an end effector including a proximal camming surface;
an elongate shaft including a hollow chamber within and a frame aligned with the camming surface of the end effector;
an articulation joint pivotally attaching the end effector to a distal end of the elongate shaft, the pivot attachment positioned distal to the proximal camming surface of the end effector;
a bending member located within the hollow chamber of the shaft and bendable therein, the bending member having a proximal end attached to the elongate shaft and a distal end slidingly engaged to the proximal camming surface of the end effector;

differential actuators comprising a first and a second fluidic actuating bladders opposingly positioned within the hollow chamber of the shaft against the bending member located therebetween, the first and a second fluidic actuating bladders proximal to the camming surface of the end effector; and an articulation control actuator proximally attached to the elongate shaft and operably configured with a third fluidic bladder longitudinally coupled to the first fluid bladder and a fourth fluidic bladder longitudinally coupled to the second fluidic bladder, wherein selective actuation of the articulation control actuator in a first direction longitudinally moves fluid from one of the third and fourth fluid bladders to one of the first and second fluidic actuating bladders to selectively deflect a distal end of the bending member to articulate the end effector.

14. A surgical instrument, comprising:

an end effector including a proximal surface;

an elongate shaft including a longitudinal axis and a lateral recess therewithin, and a frame aligned with the proximal surface of the end effector;

an articulation joint pivotally attaching the end effector to a distal end of the elongate shaft, the pivot attachment positioned distal to the proximal surface of the end effector;

a bending member having a flexible shaft portion configured to flex within the lateral recess within the elongate shaft and having a proximal end attached to the elongate shaft and a distal end engaged to the proximal surface of the end effector; and a means for selectively deflecting the distal end of the bending member to bend the flexible shaft and articulate the end effector, wherein the means for selectively deflecting the distal end longitudinally transfers fluid from a proximal end of the shaft to laterally bend the flexible shaft portion in an arcuate path in a first direction to rotate a distal end of the end effector in an arcuate path in an opposite direction.

15. The surgical instrument of claim 14, wherein the means for selectively deflecting the distal end of the bending member further comprises a means for converting a lateral control motion input by user into the deflecting of the bending member.

16. The surgical instrument of claim 14, wherein the end effector comprises a staple applying assembly, the surgical instrument further comprising a handle proximally attached to the elongate shaft and operatively configured to close and fire the staple applying assembly.

* * * * *